(12) United States Patent
Harvey

(10) Patent No.: US 7,964,028 B2
(45) Date of Patent: Jun. 21, 2011

(54) METHOD AND APPARATUS FOR SELECTIVE CAPTURE OF GAS PHASE ANALYTES USING METAL β-DIKETONATE POLYMERS

(75) Inventor: Scott D. Harvey, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 43 days.

(21) Appl. No.: 12/566,949

(22) Filed: Sep. 25, 2009

(65) Prior Publication Data

US 2010/0203652 A1    Aug. 12, 2010

Related U.S. Application Data

(63) Continuation-in-part of application No. 12/367,413, filed on Feb. 6, 2009.

(51) Int. Cl.
*G01N 33/00* (2006.01)
(52) U.S. Cl. .................. 96/101; 96/413; 73/31.01
(58) Field of Classification Search ............ 95/82, 88, 95/128, 129, 141; 96/101, 108, 154, 413; 73/23.2, 23.35, 23.41, 31.01, 31.02, 863.23
See application file for complete search history.

(56) References Cited

U.S. PATENT DOCUMENTS

| 6,749,811 | B2 | 6/2004 | Murray |
| 2003/0178607 | A1 | 9/2003 | Swager et al. |
| 2006/0073607 | A1 | 4/2006 | Rose et al. |
| 2006/0127929 | A1 | 6/2006 | Swager et al. |

OTHER PUBLICATIONS

Harvey, "Molecularly imprinted polymers for selective analysis of chemical warfare surrogate and nuclear signature compounds in complex matrices", 2005, J. Sep. Sci, Wiley-VCH.*
Harvey, Scott D. et al., Selective gas-phase capture of explosives on metal β-diketonate polymers, Journal of Chromatography A, 1192 (2008) 212-217.
Boyd, Jonathan W. et al, Development of Molecularly Imprinted Polymer Sensors for Chemical Warfare Agents, Johns Hopkins APL Technical Digest, vol. 25, No. 1 (2004, 44-49.

* cited by examiner

*Primary Examiner* — Frank M Lawrence
(74) *Attorney, Agent, or Firm* — James D. Matheson

(57) ABSTRACT

A process and sensor device are disclosed that employ metal β-diketonate polymers to selectively capture gas-phase explosives and weaponized chemical agents in a sampling area or volume. The metal β-diketonate polymers can be applied to surfaces in various analytical formats for detection of: improvised explosive devices, unexploded ordinance, munitions hidden in cargo holds, explosives, and chemical weapons in public areas.

24 Claims, 12 Drawing Sheets

R=C$_6$H$_5$; Ligand: H$_2$(ppb)
R=CH$_3$; Ligand: H$_2$(pbb)
R=CF$_3$; Ligand: H$_2$(ptb)
R=C$_3$F$_7$; Ligand: H$_2$(dihed)

H$_2$(dihed)

METHOD AND APPARATUS FOR SELECTIVE CAPTURE OF GAS PHASE ANALYTES USING METAL β-DIKETONATE POLYMERS

CROSS-REFERENCE TO RELATED APPLICATIONS

This application is a Continuation-In-Part of U.S. application Ser. No. 12/367,413 filed 6 Feb. 2009, which application is incorporated in its entirety herein.

STATEMENT OF GOVERNMENT SUPPORT

This invention was made with Government support under Contract DE-AC05-76RLO1830 awarded by the U.S. Department of Energy. The Government has certain rights in the invention.

FIELD OF THE INVENTION

The present invention relates generally to polymer compositions for selective adsorption. More particularly, the invention relates to a process that employs metal β-diketonate polymers for selective capture of gas-phase explosives and weaponized chemical agents and other harmful vapors.

BACKGROUND OF THE INVENTION

Ultra-trace analysis of gas-phase explosives and chemical weapons is critical for many homeland security, law enforcement, customs, and military applications. For example, analytical technologies enable detection of improvised explosive devices, unexploded ordinance, munitions hidden in cargo holds, detection in clandestine laboratories, and monitoring for explosives in public areas. In addition, selective trace analysis is vitally important for post-blast forensic applications. A critical need exists for performing selective trace analysis for the presence of explosives in large-volume air samples. Volatility of most explosives is limited and, therefore, ultra-trace analysis techniques are required. Usually non-selective capture is used for concentrating target organic signatures from large volumes of air. However, this approach has the problem of concentrating matrix interferences along with the analyte of interest. Sophisticated laboratory analysis is usually required due to the complexity of the captured sample. Semi-selective, high-affinity capture is desirable to concentrate trace quantities of analyte while discriminating against the matrix background interferences. Selective capture allows a relatively clean fraction to be captured and, because of the enhanced relative purity, can lead to simplified detection. The streamlined analytical system can be made lightweight and field portable without sacrificing performance. To accomplish this goal, new polymers that provide for reproducible and specific adsorption are needed.

SUMMARY OF THE INVENTION

In one aspect the invention is a method that provides for selective capture of gas-phase explosives and weaponized chemical agents. The method includes: depositing a metal β-diketonate polymer onto a preselected surface so as to construct a structure having a suitable or preselected form that is suitable for sampling (i.e., gas-sampling structure) of airborne vapors or gas-phase agents. In use, the gas-sampling structure containing the metal β-diketonate polymer is introduced to, or placed in, a sampling area (e.g., a cargo hold), a sampling volume (e.g., a vapor chamber), or a sampling location (e.g., an airport). Explosives or weaponized chemical agents present in the sampling area or location are selectively captured on the metal β-diketonate polymer of the gas-sampling structure (e.g., gas-sampler).

In another aspect, the invention also includes a method, comprising the steps of: forming a gas-sampling structure of a preselected form that includes a metal β-diketonate polymer operatively disposed on a preselected surface that provides a preselected selectivity for the gas-phase explosive or weaponized chemical agent; introducing the gas-sampling structure into a sampling volume; and selectively binding the gas-phase explosive or weaponized chemical agent in the sampling volume on the polymer of the gas-sampling structure based on the preselected selectivity.

The metal β-diketonate polymer includes a bifunctional bridging ligand and a preselected metal ion center. β-diketonate (dionyl) groups in the bifunctional ligand cross-link with a different metal ion center, which provides polymerization and cross-linking in the metal β-diketonate polymer. Polymer selectivity toward a preselected gas-phase Lewis base analyte (e.g., explosives and weaponized chemical agents) is determined by the Lewis acidity of the polymer, which is defined both by the bridging ligand (and its associated R-groups) and the selected metal ion center. For example, electronic inductive effects provided by R-groups of the ligand can tune the acidity of the metal ion center in the polymer. In various embodiments, the metal β-diketonate polymer includes a metal ion center selected from: La(III), Eu(III), Tb(III), Cu(II), Ni(II), Zn(II), and combinations of these metal ion centers. In other embodiments, lanthanide metal ions and transition metal ions can also be used. Preferred metal β-diketonate polymers for selective capture of explosives include, but are not limited to, e.g., Cu(dihed), Ni(dihed); Zn(dihed); La(dihed); Eu(dihed); Tb(dihed); and combinations of these polymers.

Chemical warfare agents can be expected to exhibit strong chemical interactions. Thus, use of weakly acidic cations [e.g., Zn(II), Cu(II), and other weakly acidic metal cations] combined with electron-donating R-groups in the metal β-diketonate polymers can decrease Lewis acidity of the polymer sufficiently to provide these polymers with ability to selectively capture weaponized agents. Electron-donating R-groups include, but are not limited to, e.g., phenyl ($-C_6H_5$); methyl ($-CH_3$); ethyl ($-CH_2CH_3$); n-propyl; isopropyl; n-butyl; isobutyl; sec-butyl; tert-butyl, and other R-groups, including combination of these R-groups. Longer alkyl chain groups may also be suitable. In general, the longer the alkyl chain, the greater the electron density that can be donated, which in the case of chemical weapons is desirable. Thus, no limitations are intended.

Polymer ligands described herein are bifunctional ligands that are based on a p-di(alkyl-1,3-dionyl)benzene structure that includes a benzene core (or other core constituent) and two R-groups including, e.g., $-CH_3$; $-CF_3$; $-C_3F_7$; $-C_6H_5$; and combinations of these R-groups. In a preferred embodiment, the ligand is p-di(4,4,5,5,6,6,6-heptafluoro-1,3-hexanedionyl)benzene, denoted herein as the $H_2$(dihed) ligand. The preferred bifunctional ligand includes the p-di(alkyl-1,3-dionyl)benzene structure with a benzene core and two R-groups comprised of $-C_3F_7$. Other bifunctional ligands include, but are not limited to, e.g., p-di(3-phenyl-1,3-propanedionyl)benzene [$H_2$(ppb) where R=$-C_6H_5$]; p-di(1,3-butanedionyl)benzene [$H_2$(pbb) where R=$-CH_3$]; and p-di(1,1,1-trifluoro-1,3-butanedionyl)benzene [$H_2$(ptb) where R=$-CF_3$]. Other ligands envisioned for use include, e.g., analogues and derivatives of 1,7,7-trimethylbicyclo[2.2.1]heptane that comprise two β-diketonate groups in geometries that cannot complex with the same metal in the polymer. Other aromatic, cyclic, and bicyclic compounds that include β-diketonate groups in positions that do not complex with the same metal cation can also be used. No limitations are intended.

The metal β-diketonate polymer can be deposited onto a preselected surface using a variety of methods. In one method, a metal β-diketonate polymer is deposited to the surface by dip coating the surface. In one embodiment, the preselected surface is a surface of a solid-phase microextraction (SPME) fiber [e.g., a fused silica fiber (quartz)] that contains a non-polar polymer coating, e.g., PDMS. For example, a 30-μm PDMS fiber means the fused silica fiber includes a 30-μm coating of PDMS on the exterior surface. The surface can also be a filter surface, e.g., a filter comprised of deactivated quartz fiber. In various other embodiments, surfaces include inert chromatographic column support surfaces and capillary column interior surfaces. In one embodiment, the preselected surface is an inert sorbent surface that is comprised of any one of a number of diatomaceous earths or other chromatographic supports. These inert supports are typically coated with a non-polar stationary phase (e.g., PDMS) before coating with the metal β-diketonate polymer. In another embodiment, a column surface is coated with a metal β-diketonate polymer. When advantageous, the column surface can be coated with, e.g., PDMS or a hydrophobic deactivation agent prior to coating with the metal β-diketonate polymer. The method further includes the step of determining the gas-phase explosive or weaponized chemical agent captured on the polymer. In one embodiment, the invention is configured for trace level analysis of the gas-phase explosive or weaponized chemical agent, e.g., at the low parts-per-trillion to upper part-per-quadrillion (v/v) detection limit. The polymers can be incorporated into a variety of analytical formats for use. Analytical formats include, but are not limited to, e.g., stationary phases, chromatographic columns (e.g., packed chromatographic columns), capillary columns; multiple capillary arrays; sorbent tubes; sorbents; filters; solid-phase microextraction fibers (e.g., SPME and other fibers). Results described herein can also extend the invention for uses in other analytical formats. For example, in one preferred embodiment, the metal β-diketonate polymer is coated onto a preselected PDMS-coated solid-phase microextraction fiber, as described hereinabove. Captured analytes can then be determined using a variety of analytical tools and instruments.

In another aspect, the invention is also a sensor device for detection of a gas-phase explosive or a weaponized chemical agent. The sensor device includes: a metal β-diketonate polymer disposed to selectively capture a gas-phase explosive or weaponized chemical agent. Sensor formats include, but are not limited to, e.g., Surface Acoustic Wave (SAW) devices, Quartz Crystal Microbalance (QCM) devices, Surface Plasmon Resonance (SPR) devices, and microcantilever devices, and the like, or combinations of these devices. In various embodiments, detection utilized in conjunction with these sensor devices and formats includes, but is not limited to, e.g., optical detection based on alteration of polymer luminescence; electrochemical detection; microcalorimetric detection; evanescent wave-based detection, infrared absorption detection, and the like, or combinations of these detection methods and devices. No limitations are intended. Metal β-diketonate polymers used in sensor devices and associated components can be deposited using coating techniques such as spray-coating and spin-coating. No limitations are intended.

In one exemplary embodiment, metal β-diketonate polymers are deposited onto fused silica fibers that contain a PDMS layer (coating) to produce semi-selective, high-affinity polymer fibers that selectively capture explosives and weaponized chemical agents (also known as chemical weapons, or CW agents) in the gas phase at extremely low concentrations for determination and identification of these agents. In this and other formats described herein, metal β-diketonate polymers can also be applied to filters and used for large volume air sampling to selectively capture trace quantities of explosives and weaponized chemical agents and other harmful vapors for selective trace analysis and determination.

In other embodiments, the invention provides a selective coating suitable for use in capillary columns. The technology offers unique orthogonal selectivity that can be useful, e.g., for multidimensional separations. Multicapillary columns (MCCs), including arrays of MCCs, can also be prepared that provide for fast separations. MCCs also provide a capability for selective capture and concentration of targeted gas-phase analytes from air. Arrays can also be thermally ramped or stepped to elute a pure fraction of a selected analyte or selected analytes of interest. Coated MCC columns and arrays can also be used as a bundled MCC selective capture/concentration interface to sensitive and selective detection devices including, but not limited to, e.g., ion mobility spectrometers, mass spectrometers, and other analytical instruments.

In one exemplary embodiment, an MCC selective preconcentrator can be prepared. A vacuum can be pulled on one end of an MCC segment to provide sampling of the air. Flows through the sampler can be on the order of about 1 L/min. Once sampling is complete, analytes collected on the MCC segment can be thermally desorbed using precise temperature control under a flow of, e.g., helium or another inert gas. The gas containing the desorbed compounds can then transfer the relatively pure fraction to a separation column or a detection instrument. Such applications have potential for selectively capturing relatively pure analyte fractions for further analysis. Due to the relative purity of a captured fraction, subsequent analysis can be simplified and associated instrumentation can be made lightweight, smaller, and field portable without negative impacts on analytical performance.

In another embodiment, the MCC segment can be encased in a temperature-programmed GC injector. A vacuum can be pulled on the MCC segment for sampling of the air, and then the injector can be easily switched to flow helium or another inert gas for purposes of desorption and analyte transfer. This configuration can provide for precise thermal desorption, with coupled elution direct to a separation column or detector. No limitations are intended.

In a preferred embodiment described hereafter, coated capillary columns are prepared using a low boiling point azeotrope, which results in columns that can be used as capillary separation columns. The prepared columns separate explosive compounds using unique Lewis acid-base interactions that are particularly suited for multidimensional separations. In other applications, solid-phase microextraction (SPME) fibers are disclosed that have a demonstrated ability to capture and analyze TNT in a realistic bunker environment at concentrations below 3 pptv, a determination that is not accomplished using conventional poly(dimethylsiloxane) (PDMS) fibers. In yet another application described herein, deactivated quartz fiber filters impregnated with metal β-diketonate polymers can be used for selective sampling/concentration followed by direct analysis with ion mobility spectrometry (IMS). Results obtained with this sampling/analysis combination demonstrate successful gas-phase capture and analysis of hexahydro-1,3,5-trinitro-1,3,5-triazine, also known as Royal Demolition Explosive (RDX), a military-grade explosive, for the first time. Selectivity of metal β-diketonate polymers will now be described.

In another aspect, the invention also includes devices that provide selective capture of an explosive or a weaponized chemical agent from a sampling volume for detection thereof. The devices are characterized by: a metal β-diketonate polymer operatively disposed that includes a preselected metal center and at least one coordinating ligand that provides a preselected selectivity for capture or retention of the explosive or the weaponized chemical agent from the sampling volume for detection thereof. In various embodiments, the devices include packed-column devices; filter devices that include a filter component comprising the metal β-diketonate polymer impregnated thereon; capillary column devices that include a stationary phase comprising the operatively disposed metal β-diketonate polymer therein as a component thereof; multi-capillary column devices; preconcentration devices that are deployed, e.g., as a component or stage of a multi-stage instrument or configuration; fiber devices that include solid-phase microextraction (SPME) fiber coated or treated with a selective metal β-diketonate polymer; field-portable analytical devices that incorporate metal β-diketonate polymers for monitoring or sampling of air-space environments, and like devices. No limitations are intended.

DETAILED DESCRIPTION

Metal β-diketonate polymers are extremely versatile polymers, since they have a high-affinity for, and selective interactions with, explosives, weaponized chemical agents, and related compounds. These polymers can be incorporated into a variety of useful analytical formats that provide capture, detection, and determination of trace quantities of explosives and other harmful analyte vapors in a variety of analytical systems and devices. Applications further include, but are not limited to, e.g., detection of explosives in cargo holds, detection of unexploded ordinance (UXO), detection of improvised explosive devices (IEDs), detection of explosives and weaponized chemical agents in vehicles, public areas, clandestine laboratories, building ventilation systems, and other large-volume air sampling applications. The invention is also useful for sampling pre-blast and post-blast explosive vapors for forensic analysis. Other applications can be envisioned in homeland security, law enforcement, customs, the military, and in the intelligence community. No limitations are intended.

Structure of β-Diketonate Ligand

Figure 1:
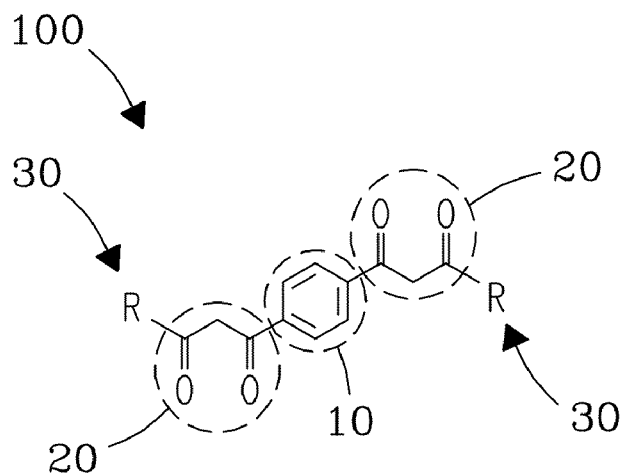
FIG. 1 shows an exemplary β-diketonate bridging ligand with selected R-group constituents used in conjunction with the invention.

FIG. 1 shows a generalized structure of a bifunctional β-diketonate ligand 100 that is a component of a metal β-diketonate polymer used in conjunction with the invention. The polymer is described further herein. The ligand includes a core molecule or constituent 10 as a center construct of the ligand to which two β-diketonate (dionyl) coordinating groups 20 are attached, e.g., in the para position. In the figure, one or more R-groups 30 are further attached to respective dionyl groups 20 of the ligand. In the figure, the exemplary ligand 100 is based on p-di(alkyl-1,3-dionyl)benzene, with benzene shown as the core molecule or constituent 10, but is not limited thereto. For example, core constituents other than benzene may also be utilized. Aromatic nuclei including, e.g., naphthalene derivatives that comprise dionyl groups positioned at the 2,6 positions, and bicyclic structures (e.g., camphor derivatives) can also be used. In addition, optically active organic compounds including, e.g., camphor (chemical formula: $C_{10}H_{16}O$) (IUPAC name: 1,7,7-trimethylbicyclo[2.2.1]heptan-2-one) and other optically active compounds can be useful core constituents to provide enantiomeric (optical isomer) selectivity. An exemplary, but non-limiting, ligand is 3,6-di(heptafluorobutanoyl)-1,7,7-trimethylbicyclo[2.2.1]heptan-2,5-dione. This optically active ligand contains bifunctional β-diketonate coordinating groups in a geometry that promotes the desired polymerization. R-groups 30 are preselected to achieve a desired inductive and/or steric effect in the metal β-diketonate polymer. Preferred R-groups 30 for selective capture of explosives include, but are not limited to, e.g., —$CH_3$; —$CF_3$; —$C_3F_7$; —$C_6H_5$, and other preselected R-groups disclosed herein. In other embodiments additional R-groups may be used that provide selective capture of weaponized chemical agents, including, but not limited to, e.g., ethyl, propyl, butyl, and higher alkyl homologues, with branched analogues being more preferred due to a greater electron donating effect. Incorporation of an optically active R-group, e.g., a sec-butyl or a 1,2,2-trimethylpropane functionality, is an alternative to using an optically active core constituent to impart enantiomeric selectivity to the metal β-diketonate polymer. All R-groups as will be selected by those of skill in the art in view of the disclosure are within the scope of the invention. No limitations are intended.

Synthesis of β-Diketonate Polymers

Metal β-diketonate polymers described herein were synthesized using p-di(4,4,5,5,6,6,6-heptafluoro-1,3-hexanedionyl)benzene ligand, denoted herein as $H_2$(dihed) ligand 100 or (dihed) ligand 100, as described, e.g., by Picker et al. [J. Chromatogr. 203 (1981) 29] and Wenzel et al. [J. Chromatogr. 463 (1989) 171]. Metal nitrates used for synthesis of metal (dihed) polymers were obtained commercially (Sigma-Aldrich, St. Louis, Mo., USA). Reagents 1,4-diacetyl benzene, ethyl heptafluorobutyrate, sodium methoxide, and diethyl ether used for $H_2$(dihed) synthesis were obtained commercially (Sigma-Aldrich, St. Louis, Mo., USA). Ethanol used for $H_2$(dihed) recrystallization was purchased (Gold Shield Chemical Co., Hayward, Calif., USA).

Figure 2:
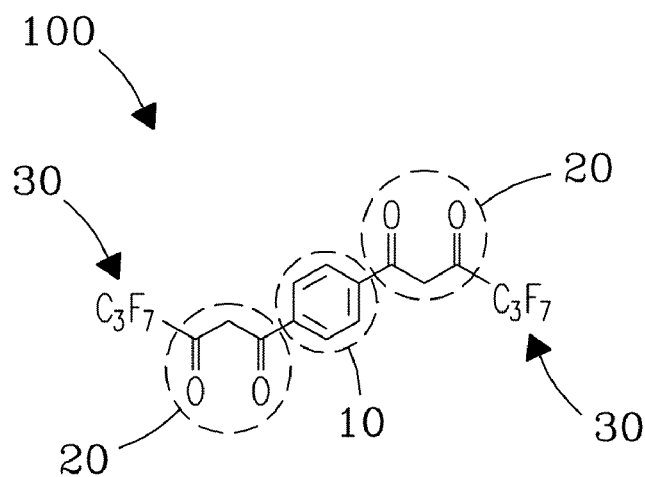
FIG. 2 shows a chemical structure of an exemplary β-diketonate ligand, i.e., $H_2$(dihed), according to a preferred embodiment of the invention.

FIG. 2 shows the structure of a preferred ligand, i.e., $H_2$(dihed) ligand 100. In the figure, the ligand includes a core constituent 10 of benzene. Two (2) dionyl groups 20 are attached to the benzene ring at the para-positions. The ligand further includes one or more terminal R-groups 30 comprised of a —$C_3F_7$ moiety 30 (i.e., —$CF_2CF_2CF_3$) that are attached to respective dionyl groups in the ligand. Electron withdrawing properties of the fluorinated R-groups accentuate the Lewis acidity of the metal ion center ligand when the ligand is incorporated in the metal β-diketonate polymer. Synthesis of the $H_2$(dihed) ligand is detailed, e.g., by Picker et al. [J. Chromatogr. 203 (1981) 29], which reference is incorporated herein. The (dihed) ligand is prepared by reaction of 2 moles of ethylheptafluorobutyrate with 1 mole of p-diacetylbenzene in the presence of sodium methoxide. The crude product is purified by repetitive recrystallization. Synthesis of the metal β-diketonate polymer involves addition of the ligand to a solution containing the selected metal cation. A small excess of metal is used and the ligand is added slowly. Product is washed to remove any excess metal ions. Analogs with different side chains (R-groups) can also be produced, e.g., as detailed by Wenzel et al. [J. Chromatogr. 463 (1989) 171], which reference is incorporated herein. Geometry of each β-diketonate group 20 in the ligand (including the respective R-groups 30) prevents coordination of both β-diketonate groups to the same metal ion. This unique geometry promotes polymerization and cross-linking to other metal centers in the polymer.

Figure 3:
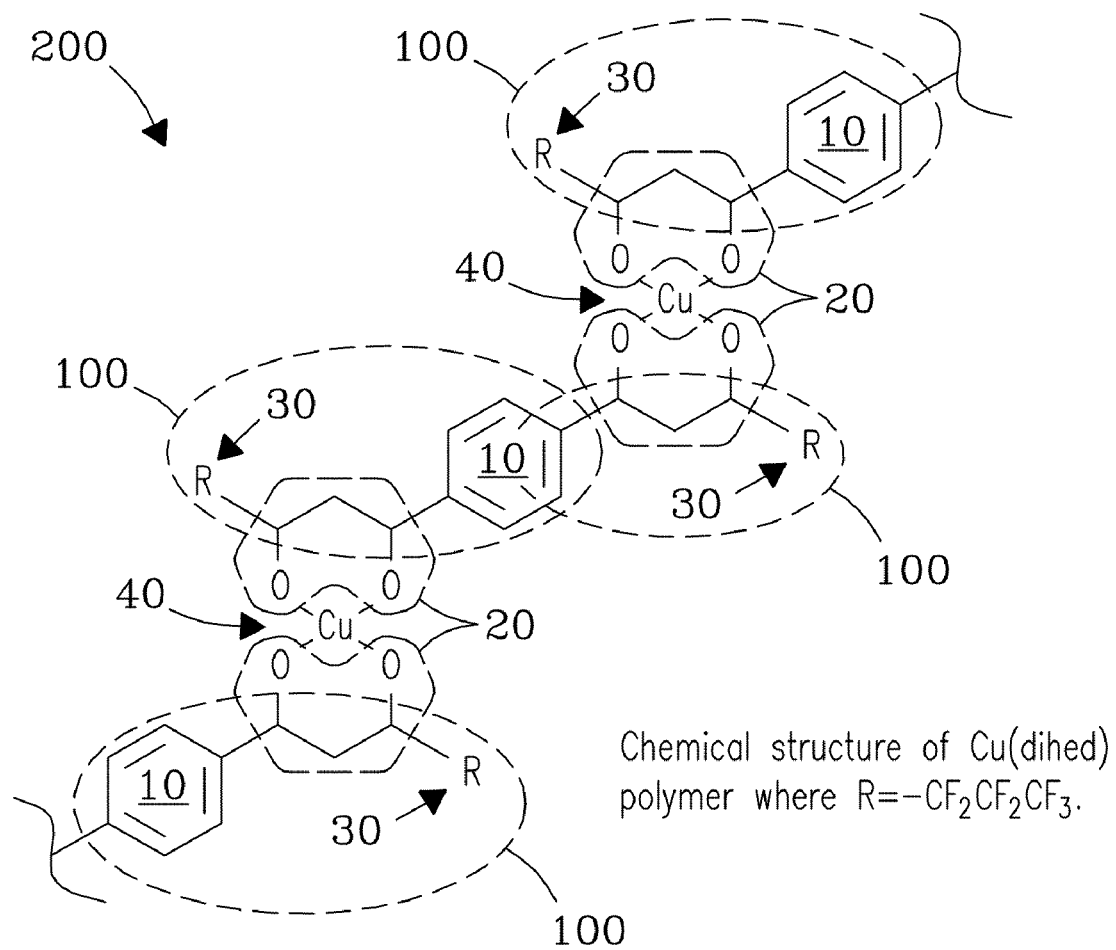
FIG. 3 shows a chemical structure of an exemplary metal β-diketonate polymer, i.e., Cu(dihed), according to another embodiment of the invention.

FIG. 3 illustrates a proposed structure of an exemplary metal β-diketonate polymer 200, i.e., Cu(dihed). The polymer includes a (dihed) ligand 100 with R-groups 30 comprised of —$C_3F_7$ (i.e., —$CF_2CF_2CF_3$). The ligand is coordinated with metal ion centers 40 [e.g., Cu(II) or another metal ion center] through dionyl groups 20 in the ligand that attach to benzene 10 as a core constituent 10. As indicated previously, this para β-diketonate bifunctionality promotes polymerization (crosslinking), since both β-diketonate groups in each ligand cannot coordinate with the same metal ion center due to geometrical considerations. Metal β-diketonate polymers include, but are not limited to, e.g., La(dihed), and Zn(dihed), described further herein. Preferred metal ion centers 40 in the metal β-diketonate polymers 200 include, but are not limited to, e.g., La(III), Eu(III), Tb(III), Cu(II), Ni(II), and Zn(II). Other lanthanide and transition metal ions can also be used. Elemental analysis of the product ensures atomic composition, ratios are consistent with hypothesized polymeric products. The Cu(dihed) polymer is prepared by adding a methanol solution containing the ligand to a cupric acetate solution. The resulting metal β-diketonate polymer (1:1 molar ratio of ligand to polymer) is then collected as a precipitate.

Preparation of the La(dihed) polymer is somewhat more complex. The ligand in the methanol solution is neutralized with aqueous sodium hydroxide to remove acidic β-diketonate hydrogen. The neutralized solution is then slowly added to a solution containing lanthanum nitrate hexahydrate dissolved in methanol. The precipitated product (metal:ligand ratio is 2:3 in this polymer) is collected by filtration, and thoroughly dried in vacuo under phosphorus pentoxide. For some lanthanide polymers, e.g., Eu(dihed), the proposed polymer structure comprises mixed ligand-hydroxo compounds. Here, average molecular weight of the Eu(dihed) polymer is estimated to be 1411 as determined by vapor pressure osmometry [see J. E. Picker and R. E. Sievers, J. Chromatogr., 203:29-40 (1981); T. J. Wenzel, L. W. Yarmaloff, L. Y. St. Cyr, L. J. O'Meara, M. Donatelli; and R. W. Bauer, J. Chromatogr., 396:51-64 (1987)].

Analytes

Figure 4:
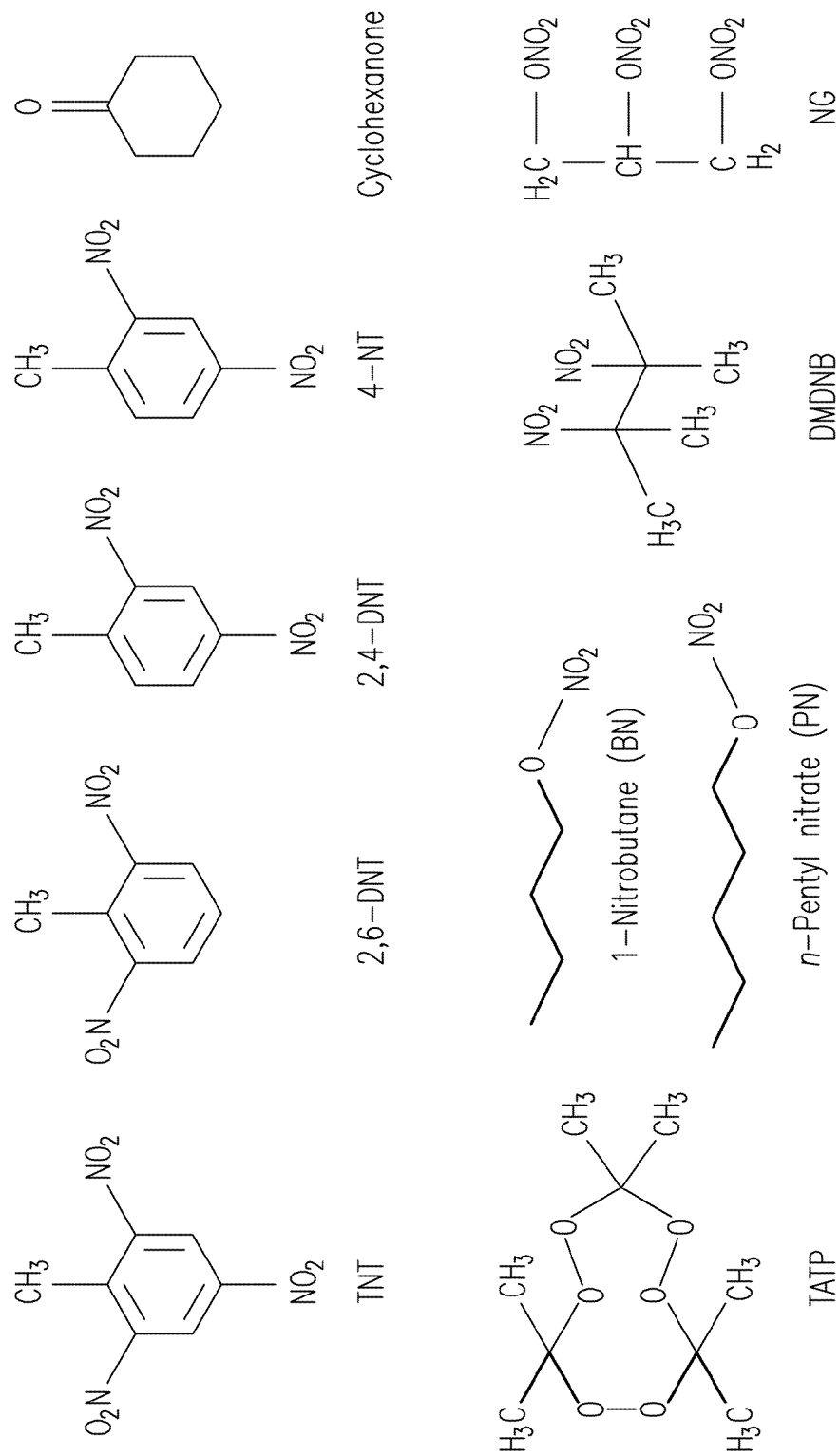
FIG. 4 shows exemplary explosives that are selectively captured by the invention.

Analytes of a national security interest include, but are not limited to, e.g., explosives, CW agents, and organic nuclear signature compounds including, e.g., tributyl phosphate. Many of these analytes have a characteristic basicity or otherwise basic character, which can be exploited to provide selective retention by the metal β-diketonate polymers. FIG. 4 shows representative chemical structures for explosives, explosive components, and related compounds captured by the invention. Explosive classes include, but are not limited to, e.g., nitroaromatics; nitrate esters; nitroalkanes; and peroxide-based explosives. Exemplary nitroaromatic explosives include, but are not limited to, e.g., 2,4,6-trinitrotoluene (TNT); 2,6-dinitrotoluene (2,6-DNT); and 4-nitrotoluene (4-NT). Exemplary nitroalkanes include nitroalkane taggants, including, but not limited to, e.g., 2,3-dimethyl-2,3-dinitrobutane (DMDNB). The term "taggant" as used herein means a chemical or physical marker that is added to an explosive as a means to trace the source, origin, or manufacturer of the explosive. DMDNB is a typical volatile compound added to explosive formulations to aid in detection. Peroxides include, but are not limited to, e.g., triacetone triperoxide (TATP). Exemplary nitrate esters include: n-butyl nitrate (BN); and n-pentyl nitrate (PN). These esters were chosen as stable analogs of explosives such as nitroglycerine (NG), ethylene glycol dinitrate (EGDN), and pentaerythritol tetranitrate (PETN). Analytical standards containing triacetone triperoxide (TATP) and trinitroglycerine (NG) dissolved in acetonitrile were obtained from AccuStandard (New Haven, Conn., USA) and Radian (Austin, Tex., USA), respectively. Due to strong interaction of acetonitrile with metal β-diketonate polymers, acetonitrile was exchanged with methylene chloride prior to analysis of these standards. Solvent exchange was accomplished by evaporating to dryness under a gentle stream of dry nitrogen and immediately reconstituting with methylene chloride. Due to instability of TATP and NG, only small quantities (<1 mg) were used in a hood equipped with a standard explosion shield. Concentration of TATP and NG in the reconstituted methylene chloride solutions was significantly lower due to evaporative losses during the exchange process. A reduced GC injection port temperature of 185° C. was used for analyses of TATP and NG to minimize degradation of the analytes. n-Butyl nitrate was synthesized as detailed, e.g., by Boschan et al. [Chem. Rev. 55:483-510 (1955)]; product purity was determined by gas chromatography/mass spectrometry (GC/MS) analysis.

Capture of aromatic nitro explosives such as TNT and 2,4,6-trinitrophenyl-N-methylnitramine (also known as: tetryl) is based on the electron rich nature of the nitro group. While nitro aromatics are often considered electron deficient, only the aromatic ring is electron deficient. Individual nitro groups are basic and thus electron rich, which provides for their selective retention on the metal β-diketonate polymers. In addition, these polymers will also capture nitrate esters (e.g., NG, EDGN, and PETN), nitramines (e.g., RDX and HMX), and peroxide (e.g., TATP) explosives. Explosives can come from various explosive classes that have different basic characteristics and, therefore, can be expected to display different retention indices on columns prepared with metal β-diketonate polymers, as described herein.

Selectivity of β-Diketonate Polymers

Metal β-diketonate polymers have a demonstrated and principal advantage of a high-affinity and selectivity for capture of explosives and CW agents. By combining this high affinity and selectivity with sensitive and selective detection, light-weight field-portable instruments can be constructed that operate with extremely low-detection limits and very high reliability. Selective sorbents provide capture of a relatively pure fraction which allows field-portable instrumentation to be constructed. And, larger volumes of air can be processed before matrix interferences become problematic. This analyte affinity and selectivity can be fine-tuned for preselected explosives and/or weaponized chemical agents. Further fine-tuning can be accomplished by exploiting steric properties of the ligand. Ability to tune the affinity makes these polymers useful for selective capture of a broad range of Lewis base target analytes suited to many governmental and industrial applications.

Tailoring of β-Diketonate Polymers for Selective Capture of Analytes

Metal β-diketonate polymers can be constructed to achieve selective capture of various analytes of interest. For example, Lewis acidity of these polymers can be tailored during synthesis for a desired application. Polymer selectivity is dictated principally by three parameters. A first parameter that affects the polymer selectivity for specific analytes is the choice of metal ion. Lewis acidity of the polymer can be preselected by selection of a suitable metal center. Each metal ion has a characteristic Lewis acidity that can be predicted by the ionic radius and charge. A trivalent cation such as La(III), e.g., will be more acidic than a divalent cation such as Zn(II) or Cu(II). Affinity for an analyte of interest can therefore be defined by selection of the metal cation. For example, β-diketonate polymers that incorporate La(III) exhibit a stronger interaction compared to Cu(II) due to the +3 charge of the La(III) ion. A second parameter that determines and/or fine-tunes Lewis acidity of a metal ion center is the electronic inductive effects of a selected ligand. Lewis acidity can be further affected by selection of an appropriate bridging ligand with selected electronic inductive effects. For example, R-groups and other side-chain groups have selected electronic inductive effects that modulate the Lewis acidity of the metal center. Exemplary R-groups include, but are not limited to, e.g., $-C_6H_5$ [resulting ligand: $H_2(ppb)$]; $-CH_3$ [resulting ligand: $H_2(pbb)$]; $-CF_3$ [resulting ligand: $H_2(ptb)$]; and $-C_3F_7$ [resulting ligand: $H_2(dihed)$]. Fluorinated ligands can also be used to withdraw electron density from the coordination sphere, which accentuates Lewis acidity of the metal center. Other ligands with selected R-groups (e.g., phenyl or alkyl groups) can donate electron density and thus decrease overall Lewis acidity. A third parameter that determines selectivity is the steric effect of a selected ligand. For example, interaction strength between the metal β-diketonate polymer and the analyte of interest can be modified using steric effects to tune the selectivity. For example, a ligand containing bulky substituents can hinder access to the metal coordination sphere by a Lewis base analyte. The analyte must first penetrate the steric shield afforded by the ligand before it can donate electron density to the metal coordination sphere. In such a case, the polymer/analyte interaction is attenuated. Parameters described herein are easily adjusted during synthesis to give a metal β-diketonate polymer with a preselected interaction strength that is selective for a given explosive or analyte for a desired application. Other selected parameters may improve capture kinetics, polymer stability, and analyte selectivity. Thus, no limitations are intended. Various analytical devices and formats that incorporate metal β-diketonate polymers will now be described.

Analytical Formats

Figure 5A:
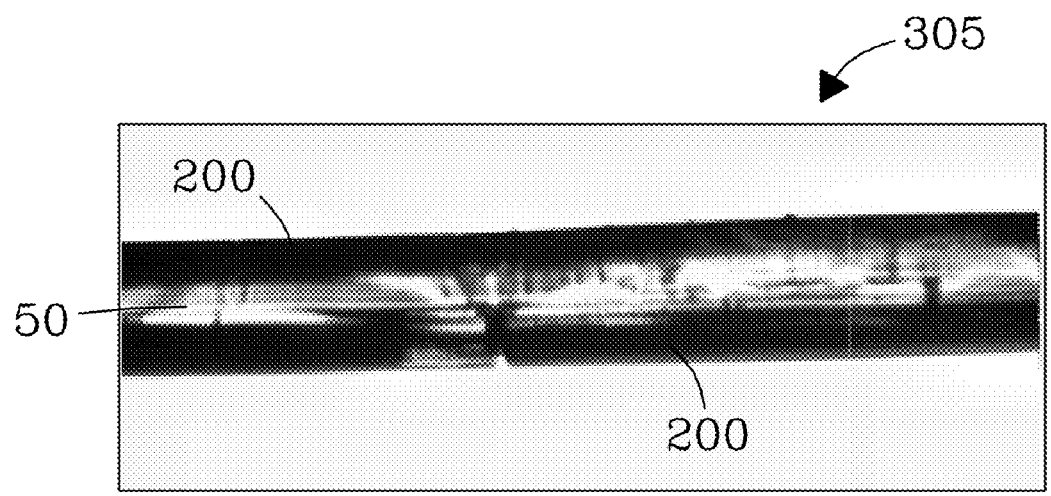
FIGS. 5a-5d show exemplary analytical device formats that incorporate metal β-diketonate polymers, according to various embodiments of the invention.

FIG. 5a shows a fiber device 305 that provides selective capture of preselected gas-phase explosives and weaponized chemical agents, according to an embodiment of the invention. Fiber device 305 includes a solid-phase microextraction (SPME) fiber 50 that is coated or otherwise treated with a metal β-diketonate polymer 200 that provides selective capture of a preselected analyte. In one embodiment, fiber device 305 can be deployed as a single stand-alone sensor for monitoring of air-space environments that may contain explosives and chemical weapons. In other embodiments, device 305 that incorporates SPME fibers coated with selected metal β-diketonate polymers can be deployed in conjunction with field-portable analytical instruments interfaced with, e.g., automated compact GC instruments for monitoring or sampling of air-space environments that may contain explosives and chemical weapons. Ultra-trace analysis of explosives in air requiring selective chromatographic preconcentration coupled with sensitive and selective detection can also be performed. SPME fibers and capillary columns coated with selected metal β-diketonate polymers described herein may also offer lower retention for analysis of strongly retained analytes that cannot be currently addressed by packed GC columns. All analytical formats and devices that incorporate SPME fibers treated with selected metal β-diketonate polymers are within the scope of the invention.

Figure 5B:
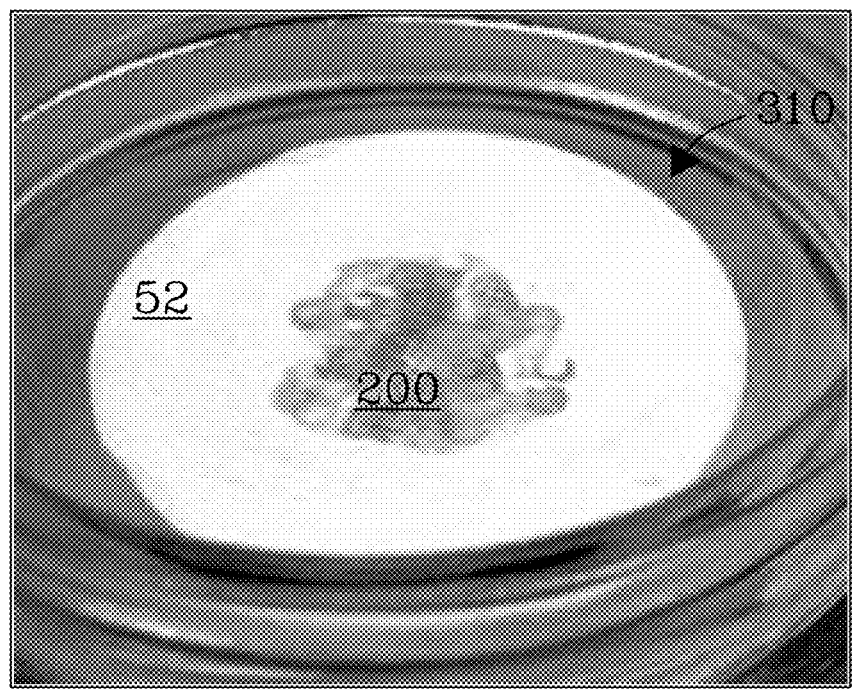

FIG. 5b shows a filter device 310, according to another embodiment of the invention. Device 310 includes a quartz filter 52 composed of a deactivated quartz fiber that is impregnated, coated, or treated with a metal β-diketonate polymer 200. Polymer 200 is selective for, and provides capture of, a preselected gas-phase explosive or weaponized chemical agent, or like analyte. Filter device 310 can be interfaced to, and/or used in conjunction with, various analytical instruments including, but not limited to, e.g., ion mobility spectrometry (IMS) instruments, mass spectrometry (MS) instruments, and other analytical instruments that provide for detection and determination of the analyte captured by, and desorbed from, the filter device.

Figure 5C:
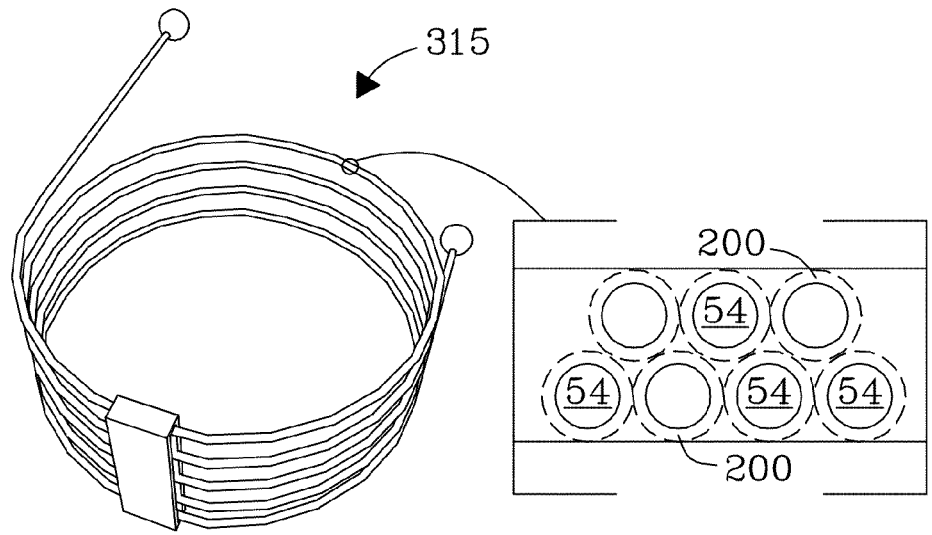

FIG. 5c shows a gas chromatography column device 315, according to yet another embodiment of the invention. In the figure (inset), column device 315 is packed with a preselected sorbent 54 that is coated or otherwise treated with a metal β-diketonate polymer 200. Polymer 200 provides selective retention of preselected explosives, weaponized chemical agents, or like analytes. Sorbent 54 is preferably prepared in two steps, but the method is not intended to be limiting. In a first step, the selected sorbent 54 [e.g., a diatomaceous earth (e.g., CHROMOSORB W HP®, Sigma-Aldrich, St. Louis, Mo., USA)] is slurried in a selected solvent (e.g., methylene chloride) that contains a quantity of a poly(dimethylsiloxane) elastomer (e.g., SE-30® polymer, Supelco, Bellefonte, Pa., USA) dissolved therein. The methylene chloride solvent is removed using a rotary evaporation apparatus leaving a film of SE-30® polymer on the diatomaceous earth. In a second step, a slurry containing the SE-30®-coated diatomaceous earth is prepared in a different solvent (e.g., methanol solvent) that does not dissolve the SE-30® deposited during the first step. Next, a selected metal β-diketonate polymer is added to the slurry. If a lanthanide(dihed) polymer is used, the polymer dissolves in methanol. If another polymer is selected, e.g., Zn(dihed) or Cu(dihed), the polymer will not dissolve but will form a suspension of small particles in the slurry. Methanol used herewith is removed by rotary evaporation, leaving the metal β-diketonate polymer deposited on the SE-30®-polymer-coated sorbent. Because coating thickness is difficult to determine, stationary phase deposition is reported on a weight percent basis. In exemplary tests, a 5% (w/w) metal β-diketonate loading on a 3% (w/w) SE-30®-coated CHROMOSORB W HP® sorbent was used, although no limitations are intended. Size of sorbent particles and quantity of sorbent is also not limited.

Figure 5D:
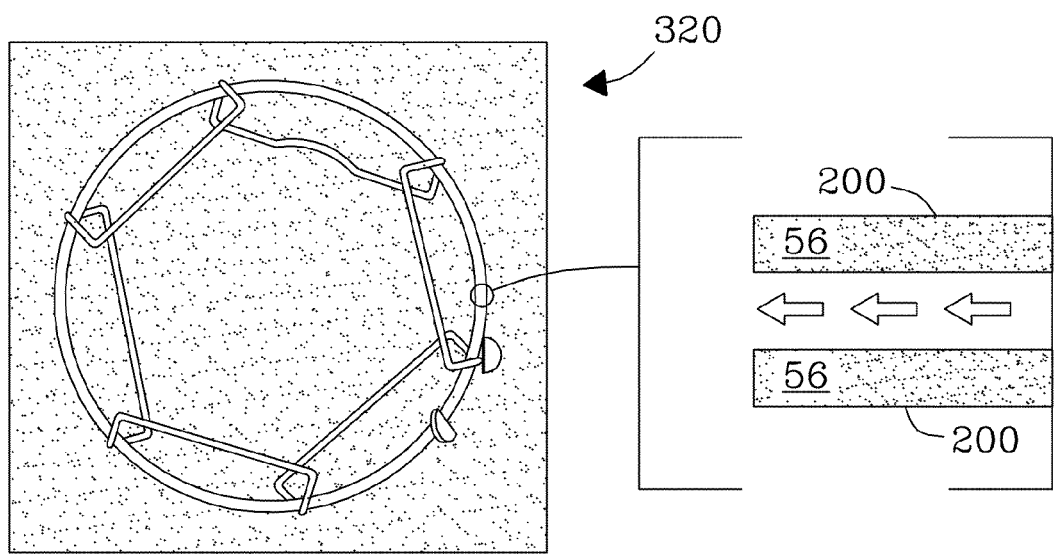

FIG. 5d shows a capillary column device 320, according to still yet another embodiment of the invention. In the figure (inset), column device 320 includes a stationary phase 56 composed of a metal β-diketonate polymer 200. Stationary phase 56 is deposited on the interior surface of the capillary column. Polymer 200 in stationary phase 56 provides selective retention of preselected explosives, weaponized chemical agents, or like analytes within the capillary column. Column parameters including, e.g., length, diameter, and retention times are not limited, as will be understood by those of ordinary skill in the art. Capillary columns coated with these polymers can be used as orthogonal stationary phases for multi-dimensional separations. In one embodiment described further herein, a solution, containing a selected metal. β-diketonate polymer [e.g., La(dihed)] is (statically) coated into a deactivated fused silica column. Multi-capillary column (MCC) devices are also described herein that include, e.g., multi-capillary arrays or bundled capillaries (e.g., ~1000×40 μm I.D. capillaries) that provide a honeycomb cross-section array of small capillary columns each having, e.g., an approximate 2 mm-outer diameter (O.D.). These devices can be used as an interface to an analytical instrument. For example, multi-capillary columns (MCCs) can include stationary phases composed of a coating of metal β-diketonate polymers to provide for fast GC separations. Alternatively, MCCs can be bundled to form an interface for selective concentration and subsequent introduction of analytes into analytical instrumentation such as IMS. Other field-portable analytical systems and devices that include these polymers in other promising analytical formats are envisioned. For example, the invention is compatible for uses in sensor development based on a number of transduction principles including, but not limited to, e.g., changes in luminescence that occur upon interaction of luminescent metal β-diketonate polymers [e.g., Eu(III), Tb(III)] with Lewis base analytes such as explosives. Another analytical device that incorporates metal β-diketonate polymers includes, e.g., molecularly imprinted polymer devices. All analytical formats employed by those of ordinary skill in the art in view of the disclosure are within the scope of the invention. No limitations are intended.

Devices of the invention provide selective capture of selected analytes including, e.g., explosives and weaponized chemical agents (e.g., nerve agents) that can be analyzed and identified. In particular, these devices find application in detection of explosives in cargo holds, detection of unexploded ordinance (UXO), detection of improvised explosive devices (IEDs), detection of explosives and weaponized chemical agents in vehicles, public areas, clandestine laboratories, building ventilation systems, and other large-volume air sampling areas. The invention is also useful for sampling pre-blast and post-blast explosive vapors for forensic analysis. These devices can also be used for other related applications in homeland security, law enforcement, customs, the military, and in the intelligence community. Thus, no limitations are intended.

Capacity Factor

Capacity factor (k') is a measure of the retention ability of a chromatographic column for an analyte of interest. The capacity factor is determined as the ratio of the difference between the analyte retention time ($t_R$) and the column dead time ($t_O$) divided by the dead time ($t_O$), as given by Equation [1]:

$$k' = \left(\frac{t_R - t_o}{t_o}\right) \quad [1]$$

Dead time ($t_O$) is a geometrical parameter that is independent of the types of analytes and the mobile phase. Methane is often used in gas chromatographic studies to determine the dead time for a selected column. Reduced retention time ($t_R$-$t_O$) is the time required to elute an analyte minus the time required for a non-retained compound to traverse the column. TABLE 1 lists capacity factors for selected explosives at selected temperatures.

TABLE 1

Capacity factors and capacity factor ratios from analysis of explosives and related compounds on columns that contain metal β-diketonate polymers.

| Capacity Factor Ratio/Compound (at ° C.) | $K_{control}'$ | $k_{Zn(dihed)}'/k_{control}'$ | $k_{Cu(dihed)}'/k_{control}'$ | $k_{La(dihed)}'/k_{control}'$ |
|---|---|---|---|---|
| TNT (190° C.) | 1.89 | 1.74 | 2.45 | 12.54 |
| 2,6-DNT (170° C.) | 1.45 | 1.87 | 2.82 | 21.93 |
| 4-NT (165° C.) | 0.71 | 2.28 | 4.91 | 36.62 |
| BN (75° C.) | 1.18 | 4.05 | 7.74 | a |
| PN (75° C.) | 2.46 | 5.05 | 8.38 | a |
| DMDNB (110° C.) | 3.05 | 4.58 | a | a |
| TATP (90° C.) [b] | 4.96 | 2.18 | a | a |

[a] Compound either decomposed or was too strongly retained to elute.
[b] Elution of intact analyte could be verified by MS.

Compounds shown in TABLE 1 represent a broad range of volatile explosive compounds including representatives from the nitro aromatic (TNT, 2,6-DNT, and 4-NT), nitrate ester (BN and PN), peroxide-based (TATP), and the taggant (DMDNB) classes. In general, interactions between the metal β-diketonate polymers and explosives increased in the following order: Control <Zn(dihed)<Cu(dihed)<<La(dihed). Interaction strengths for the [La(dihed)] ligand, i.e., La(III) complex of p-di(4,4,5,5,6,6,6-heptafluoro-1,3-hexanedionyl)benzene, shows 13-37 time greater retention for nitro aromatic compounds compared to a control column (identical column but lacking the 5% loading of the metal β-diketonate polymer). Nitrate esters, the peroxide explosive triacetone triperoxide, and the taggant 2,3-dimethyl-2,3-dinitrobutane were too strongly retained to elute from the La(dihed) column. These compounds were observed to elute using a less retentive Cu(dihed) or Zn(dihed) column.

In general, capacity factor studies demonstrated a robust retention of target explosives on columns containing metal (dihed) polymers compared to control columns. Capacity factor experiments described hereinabove also demonstrated that metal β-diketonate polymers exhibit a strong affinity toward explosives. However, before a candidate metal β-diketonate polymer is deemed suitable for use, its selectivity relative to matrix interferences should be demonstrated. For example, certain materials, like carbon-based sorbents, while expected to show strong affinity in general toward organic compounds including explosives, the selectivity relative to background organic matrix components is not expected to be high. Thus, overall properties are not advantageous for selective capture. Experiments described hereafter investigated the selectivity of various metal β-diketonate polymers relative to matrix background compounds using a chromatographic measurement termed the Kováts index.

Kováts Retention Index

The Kováts (retention) index (I) quantifies relative elution times and retention times of compounds on different stationary phases. The Kováts index is experimentally determined by bracketing an analyte of interest between retention times for two n-alkanes that differ in size by one methylene unit, i.e., between a shorter (smaller) alkane and a longer (larger) alkane. The Kováts index is independent of many chromatographic variables including, e.g., column dimensions, column format (packed or capillary), and carrier gas flow rate. The isothermal Kováts index (I) involves a linear relationship between values of [log($t_r'$)] and the number of carbon atoms in the organic compound or molecule, as given by Equation [2]:

$$I = 100 \times \left[ n + (N-n) \frac{\log(t'_{r(unknown)}) - \log(t'_{r(n)})}{\log(t'_{r(N)}) - \log(t'_{r(n)})} \right] \quad [2]$$

Here, (n) is the number of carbon atoms in the smaller n-alkane; (N) is the number of carbon atoms in the larger n-alkane; and ($t_r'$) is the adjusted retention time. The Kováts index is ideally suited to define selectivity since the index determines retention relative to non-polar hydrocarbons (n-alkanes). Hydrocarbons are major matrix interferences encountered in large-volume air samples. In exemplary tests, the Kováts index was used to assess the retention selectivity of various metal β-diketonate polymers [i.e., (dihed) polymers] for TNT, an exemplary gas-phase explosive. Experiments were conducted at the same temperature to allow direct comparison of Kováts index values. n-Alkane marker mixtures were commercially available (Polyscience Corporation, Niles, Ill., USA) and individual n-alkanes were purchased (Alltech, Deerfield, Ill., USA). Results are presented in TABLE 2.

TABLE 2

Kováts index values for exemplary metal (dihed) columns.

| COLUMN | TEMPERATURE (° C.) | KOVÁTS INDEX (TNT) |
|---|---|---|
| Control | 200 | 1662 |
| Cu(dihed) | 200 | 1784 |
| La(dihed) | 200 | 2124 |

Kováts values of 1600 and 1700 correspond to a retention time for n-alkanes n-$C_{16}$ and n-$C_{17}$, respectively. A Kováts increment of 100 corresponds to a retention time for a methylene unit ($CH_2$). A Kováts value of 1662 for TNT indicates that TNT has a retention time between an n-$C_{16}$ and an n-$C_{17}$ alkane. From TABLE 2, the La(dihed) column exhibits a selectivity for TNT that is 4.62 methylene units greater than that of the control [i.e., (2124 minus 1662)/100=4.62]. This result demonstrates that La(dihed) exhibits a very high selectivity for TNT relative to nonpolar hydrocarbons. In general, metal β-diketonate polymers display ideal characteristics of both high affinity (as indicated by the capacity factors) and high selectivity (as indicated by Kováts index values) toward explosives. Kováts index results are particularly relevant since hydrocarbon components are known to be principal matrix interferences in air samples.

Proof-of-principle experiments will now be described that employ various and exemplary analytical formats incorporating metal β-diketonate polymers including, but not limited to, e.g., solid-phase micro-extraction (SPME) fibers, stationary phases, chromatographic columns (e.g., packed chromatographic columns), sorbents packed in tubes, solid-phase microextraction coatings, and a variety of sensor formats.

Analysis of Explosives

Figure 6:
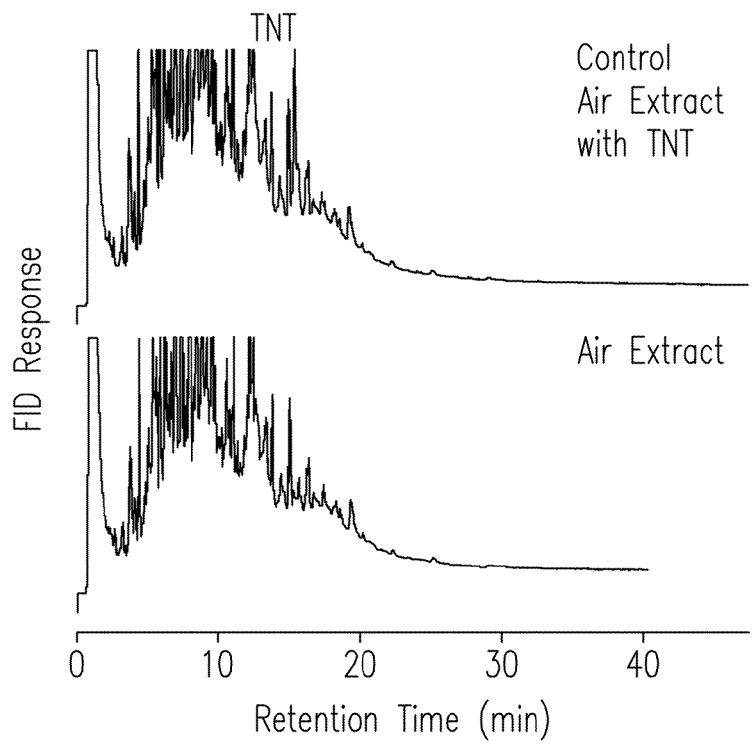
FIG. 6 compares chromatograms for a TNT-spiked air extract concentrate and a non-spiked air extract concentrate on a column packed with a control support material.
Figure 7:
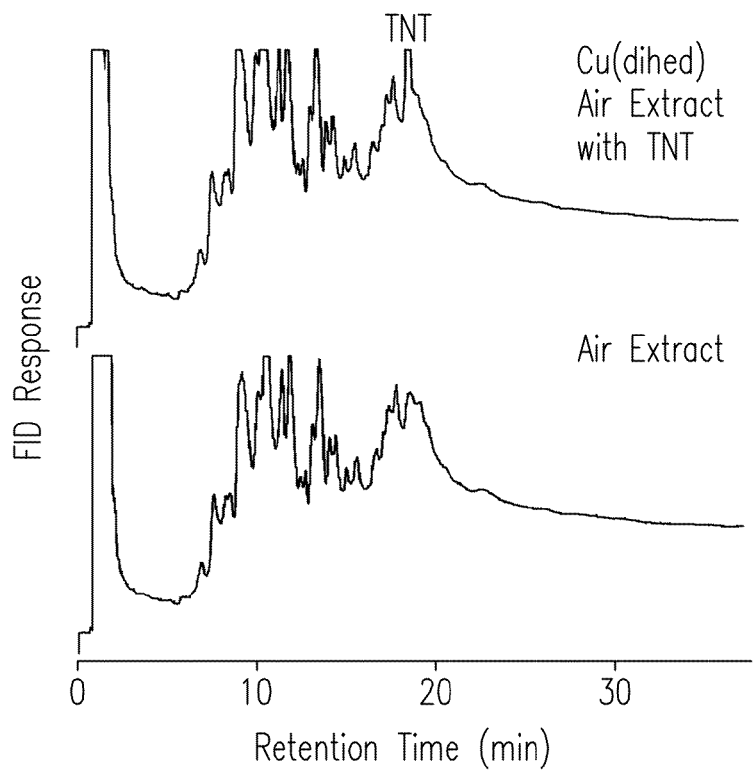
FIG. 7 compares chromatograms for a TNT-spiked air extract concentrate and a non-spiked air extract concentrate eluted on a chromatographic column containing a support that included a Cu(dihed) metal β-diketonate polymer.
Figure 8:
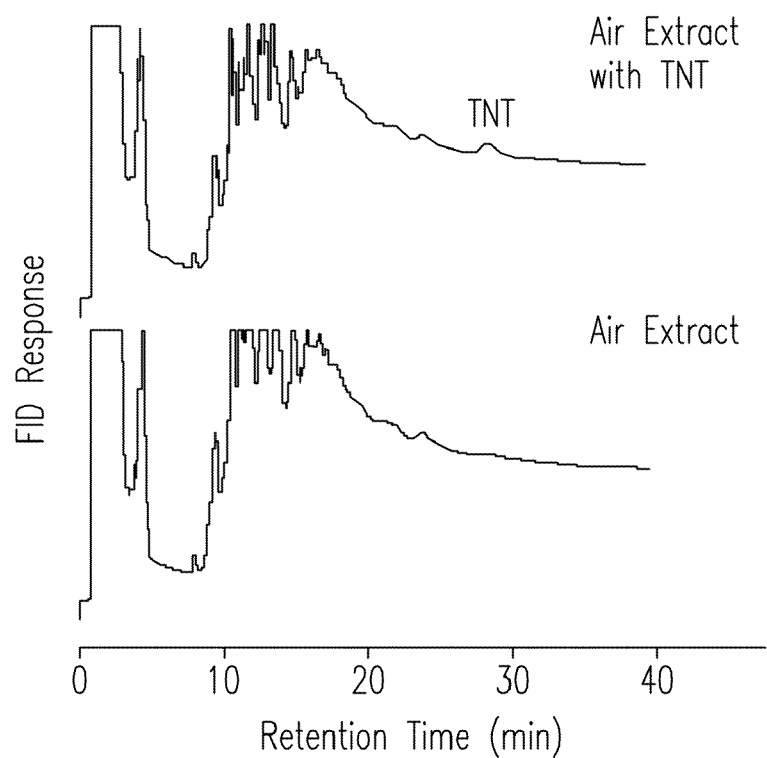
FIG. 8 compares chromatograms for a TNT-spiked air extract concentrate and a non-spiked air extract concentrate eluted on a chromatographic column containing a support that included a La(dihed) metal β-diketonate polymer.
Figure 9:
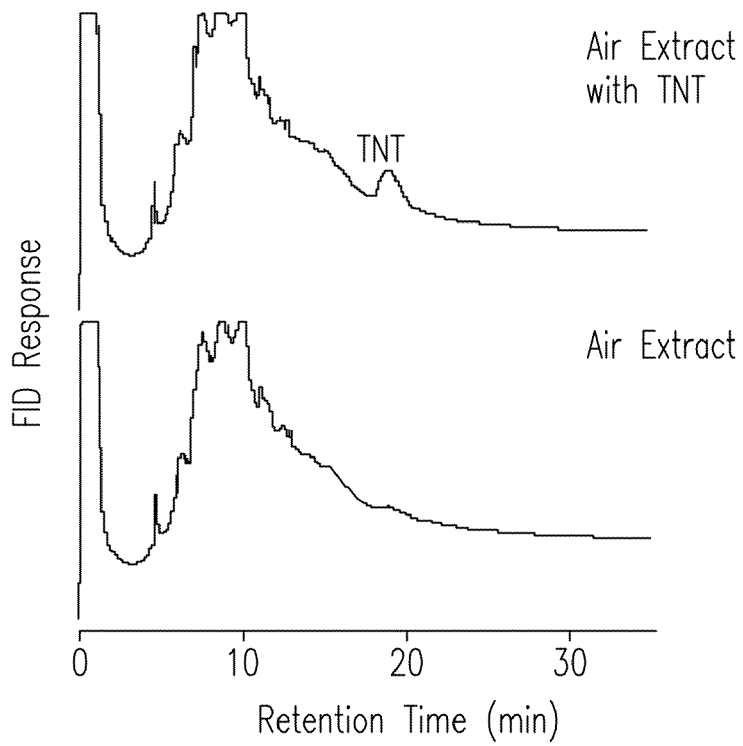
FIG. 9 compares chromatograms for a TNT-spiked air extract concentrate and a non-spiked air extract concentrate eluted on a chromatographic column with a decreased column length and a support that included a La(dihed) metal β-diketonate polymer.

Proof-of-principle experiments were performed using temperature programmed runs to measure ability of metal β-diketonate polymers to selectively retain TNT relative to the matrix interferences. Separations shown in FIGS. 6-8 used a temperature program that started at 50° C. for 2 minutes, followed by a 10° C./minute ramp to a final temperature of 200° C. Control columns (8 ft.×⅛ in. O.D.) were packed with CHROMOSORB W HP® (Sigma-Aldrich, St. Louis, Mo., USA), a diatomaceous earth, used as an inert support material, that included a 3% (w/w) loading of PDMS. Experimental columns were prepared using the same support material as the controls which additionally included a 5% loading (w/w) of a selected metal β-diketonate polymer. TNT-spiked air extract concentrate samples and non-spiked air samples were compared using a column containing selected metal β-diketonate polymers against a control column (identical column but lacking a 5% loading of the selected metal β-diketonate polymer). TNT was spiked to correspond to an extrapolated air concentration level of 47-ppt (v/v). In one embodiment, the column included Cu(dihed) polymer. FIG. 6 compares chromatograms for a TNT-spiked air extract concentrate (top) and a non-spiked air extract concentrate (bottom) eluted on a control column (no metal β-diketonate polymers). In the figure, TNT has a standard retention time of 15.30 min (control). In the control column, TNT explosive elutes in an area of considerable matrix interference, which is reflected in the recovery value of 138% calculated from the integrated peak area referenced to a 100% standard. The recovery value is high due to co-elution of interferences. FIG. 7 shows the separation achieved under temperature programmed conditions on a column loaded with Cu(dihed). In this column, retention time for TNT was 18.74 min. The Cu(dihed) column has intermediate retention for explosives (see TABLE 1). As shown, the explosive elutes in the midst of numerous matrix components. The calculated recovery of 157% reflects the presence of severe co-eluting interferences. Inspection of the chromatograms indicated that phases with yet higher selectivity for TNT would be advantageous for this application. Based on these Cu(dihed) range-finding experiments, the TNT separation was repeated on a La(dihed) column. FIG. 8 compares chromatograms for a TNT-spiked air extract concentrate (top) and a non-spiked air extract concentrate (bottom) eluted on a column containing a 5% (w/w) loading of La(dihed) polymer, another exemplary metal β-diketonate polymer. In the top chromatogram, the injection corresponds to 200 L of air that contains an extrapolated 47 ppt (v/v) of TNT. Chromatograms show TNT elutes with a retention time of 30.01 min. TNT is also retained such that it elutes well beyond any matrix interferences. The near-quantitative recovery of 110%, as well as inspection of the TNT retention window in the non-spiked sample (bottom chromatogram), indicate a complete lack of matrix interferences. Use of the La(dihed) polymer clearly provides adequate selectivity for successful analysis of TNT in air samples. However, column bleed was observed at the upper temperature of 200° C. Column bleed observed in the figure is due to limited thermal decomposition of the stationary phase at elevated temperatures. These decomposition products can "bleed" from the column causing an elevated baseline. In general, use of metal β-diketonate polymers as stationary phases in columns is preferably limited to a temperature maximum of about 180° C. Since the stationary, phase contains a heavily fluorinated ligand, decomposition products can be expected to cause severe interferences with certain detection modes sensitive toward halogenated species (e.g., electron capture detection, negative chemical ionization mass spectrometry, or ion mobility spectrometry). The column bleed can be reduced, however, using strategies such as, e.g., chemical cross-linking, covalent incorporation of the metal β-diketonate polymer into, e.g., the poly(dimethylsiloxane) (PDMS) stationary phase, or simple approaches such as shortening the column length. The latter approach is effective since there is less stationary phase to contribute to column bleed and, in addition, lower temperatures can be used to accomplish analyte elution. As noted herein, the selective retention value (i.e., Kováts index) of TNT is larger than required to separate the explosive from matrix components. Therefore, the La(dihed) column can be shortened as a strategy for reducing column bleed. Preliminary tests on a shorter column demonstrated that a reasonably sharp TNT peak and a significant decrease in column bleed was observed using a temperature ramp that stopped at a maximum temperature of 180° C. rather than 200° C., but is not limited thereto. All temperature ramping processes and temperature profiles as will be selected by those of skill in the chromatographic arts in view of the disclosure are within the scope of the invention. FIG. 9 compares chromatograms for a TNT-spiked air extract concentrate (top) and a non-spiked air extract concentrate (bottom) that were eluted on a chromatographic column containing La(dihed) polymer that had a decreased column length (2 ft.×⅛ in. O.D.), eluted using a modified temperature program. In the figure, selective retention of TNT (retention time of 19.15 min) is still adequate to pull this compound away from the majority of matrix interferences, which is reflected by the calculated recovery of 113%. Shortening the column from 8 ft. to 2 ft. had the desirable effect of dramatically decreasing the column bleed. With a decrease in column bleed, more selective and sensitive detection could be initiated. Studies described hereinabove used metal (dihed) polymers coated on inert supports which were then packed into gas chromatographic columns. Although effective for separation of TNT in an air extract concentrate, the packed column format was not appropriate for some compounds due to excessively strong interactions. For example, packed-column GC using La(dihed) was not successful for analyzing nitrate esters, DMDNB, or TATP. Similarly, interactions on Cu(dihed) were too strong for analysis of TATP and DMDNB. Zn(dihed) was one phase that allowed analysis of all the target compounds. Other formats may also offer attenuated interaction strengths and, therefore, allow analysis of target analytes that are too strongly retained on packed columns. Thus, no limitations are intended.

SPME Fibers Coated with Metal β-Diketonate Polymers

Sampling experiments were conducted using solid-phase microextraction (SPME) fibers including, e.g., fused silica fibers, or other solid-phase microextraction fiber, coated with non-polar polymers, e.g., polydimethylsiloxane (PDMS). In various embodiments, SPME fibers are coated with at least one selected metal β-diketonate polymer, and then used for sampling of gas-phase explosives. Coated fibers are then placed at a selected location (e.g., an airport location) to selectively capture gas-phase analytes. The prepared fibers thus allow for sampling of preselected gas-phase or airborne explosives at that location. Locations are not limited. In an exemplary test, PDMS fibers were coated with a La(dihed) polymer. Fibers were coated by dipping the PDMS fiber into a concentrated solution containing the dissolved metal β-diketonate polymer [e.g., ~250 mg La(dihed)/mL methanol], which formed a fairly uniform La(dihed) layer atop the non-polar PDMS fiber. After thermal conditioning (e.g., 180° C. for 30 min. under helium flow), fibers were ready for use. Initial tests exposed fibers overnight to saturated TNT air samples using a saturation tank (a flake of military-grade TNT in a capped vial). After sampling, coated fibers were analyzed by GC/MS. Results are presented in TABLE 3.

TABLE 3

Quantity of TNT captured on the La(dihed) experimental and control fibers exposed overnight to a saturated TNT vapor.

| FIBER | TNT (nanograms on fiber) |
| --- | --- |
| 7-μm La(dihed) | 12.33 |
| 7-μm (control) | 3.61 |
| 7-μm La(dihed) | 8.21 |
| 7-μm (control) | 2.42 |
| 30 μm La(dihed) | 16.06 |
| 30-μm (control) | 7.38 |
| 30 μm La(dihed) | 12.22 |
| 30-μm (control) | 6.04 |

Results show a prominent enhancement in the quantity of captured TNT on the metal β-diketonate-coated SPME fiber compared to PDMS controls. In particular, the La(dihed)-coated fibers exhibit a greater affinity for TNT relative to the PDMS controls. La(dihed) fibers also captured a greater quantity of 2,4-DNT (a TNT impurity), than did the control (data not shown). 30-μm fibers coated with La(dihed) picked up more TNT on an absolute basis than the 7-μm coated fibers. However, 7-μm fibers displayed better performance than 30-μm fibers relative to the PDMS controls. The superior performance of the 7-μm fibers is attributed to the fact that these fibers are easier to coat—a property that resulted in a larger La(dihed) phase volume compared to the 30-μm fibers (as determined by scanning electron microscopy). Coated fibers were also tested in an explosives bunker prepared from a cargo container ("seatainer") that contained a steel ammunition magazine. Air was sampled in both the magazine and bunker room. Fibers were allowed to sample air for 48 to 72 hrs. Early GC/MS experiments identified TNT and 2,4-DNT on fibers used to sample air in the magazine using retention times and mass spectra. Since the bunker contained small amounts of 2,4-DNT in addition to bulk TNT, the 2,4-DNT may have originated from the neat 2,4-DNT sample or as an impurity in the bulk TNT. To increase sensitivity for 2,4-DNT and TNT in subsequent analysis runs, fibers were analyzed under Selected Ion Monitoring (SIMS) conditions. TABLE 4 summarizes results.

TABLE 4

Quantity of TNT captured on the La(dihed) experimental and the PDMS control fibers when exposed 48 to 72 hrs to air in an explosives bunker.

| SAMPLING LOCATION | FIBER | 2,4-DNT (picograms on fiber) | TNT (picograms on fiber) |
|---|---|---|---|
| Magazine | 7-μm La(dihed) | 849.4 | 231.4 |
| Magazine | 7-μm (control) | 42.2 | 13.7 |
| Magazine | 30 μm La(dihed) | 848.5 | 65.5 |
| Magazine | 30 μm (control) | 100.3 | 22.3 |
| Seatainer (room air) | 7-μm La(dihed) | 14.5 | 6.9 |
| Seatainer (room air) | 7-μm (control) | 1.70 | <1.0* |
| Seatainer (room air) | 30 μm La(dihed) | 10.7 | 2.4 |
| Seatainer (room air) | 30 μm (control) | 2.5 | ≦1.0** |

*Below Detection Limit
**Analyte is about at the detection limit

Figure 10:
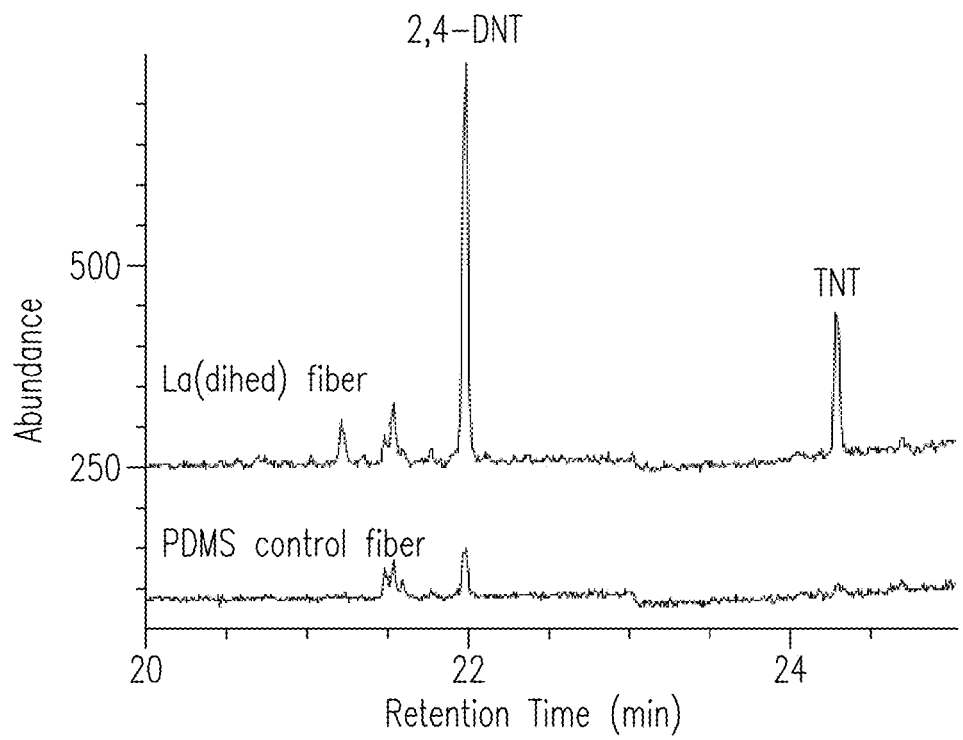
FIG. 10 presents chromatograms showing elution of selected explosives that were selectively concentrated on a La(dihed)-coated SPME fiber or a PDMS coated control fiber.

Results show a detection limit of about 1 picogram (pg) (S/N=3) was achieved for each analyte using this approach. FIG. 10 presents chromatograms that compare analyses of bunker room air on a La(dihed) coated fiber (top) to a 7-μm PDMS control fiber (bottom). Analysis proceeds by thermal desorption of the SPME fiber, separation of the components by capillary GC, and detection by SIMS. Results show the advantage of analyzing TNT and 2,4-DNT in the cargo container environment using the high affinity semi-selective La(dihed) polymer compared to non-selective PDMS controls. La(dihed) offers selective capture with much higher affinity for the targets (2,4-DNT and TNT) than non-selective PDMS controls. Detection limit in this analysis was approximately 1 picogram of explosive (S/N=3). Results show that 7-μm La(dihed) fibers captured 20 times the amount of 2,4-DNT and 17 times the quantity of TNT compared to the PDMS control when sampling air within the magazine. In room air, concentration of TNT was estimated to be far less than 3 ppt (v/v). The 7-μm La(dihed) fiber captured 9 times the amount of 2,4-DNT relative to the PDMS control fiber. TNT is well below the detection limit in the bunker room air for analysis using the PDMS control; TNT is not visible in the chromatographic trace. In contrast to the PDMS control, sampling under identical conditions with La(dihed) fibers resulted in a strong signal for TNT. These results are highly significant, since conventional PDMS fibers are often used for ultra-trace analysis. Furthermore, the sampling scenario determines TNT at concentrations and conditions required for analysis of cargo holds for hidden explosives. Therefore, results are highly relevant. The La(dihed) fibers can also be used for multiple runs. Several fibers were used for more than 12 sampling/analysis cycles with no observed degradation in performance. Fibers can be refurbished simply by rinsing the spent (used) fibers in methanol to remove the old La(dihed) coating and applying a fresh La(dihed) coating, e.g., by dipping again in a concentrated methanol solution containing the La(dihed), and drying, e.g., by evaporating solvent in an 80° C. oven for 4 min, and thermally conditioning the coated fibers at 180° C. for 30 min under helium flow. No limitations are intended.

Quartz Fiber Filters Coated with Metal β-Diketonate Polymers

Another analytical format suitable for capture of explosives is to apply a solution (or suspension) containing a selected metal β-diketonate polymer to a deactivated quartz fiber filter. Loading of the metal β-diketonate on the filter is up to the limit of solubility in the selected solvent. Thus, no limitations are intended. A typical loading includes, but is not limited to, e.g., about 1.5% by weight. Analytes (e.g., explosives) can then be collected directly on the impregnated filter. Analytes on the filter can then be thermally desorbed into a sensitive and selective detector including, e.g., an ion mobility spectrometer for detection of the desorbed compounds. Capture of explosives on coated filters or fibers can be selective to a single class of analyte (e.g., nitrate esters), or can be semi-selective to capture more than one analyte or class of analyte (TNT and nitrate esters). In an exemplary test described further in Example 7, deactivated quartz fiber filters impregnated with selected metal β-diketonate polymers have been used for selective sampling/concentration followed by direct analysis with ion mobility spectrometry (IMS). Results obtained with this sampling/analysis combination demonstrate gas-phase capture of hexahydro-1,3,5-trinitro-1,3,5-triazine (RDX) for the first time. Results further demonstrate the potential of such applications for uses in streamlined, field-deployable analytical approaches/instruments that involve selective capture of explosive materials with direct analysis by ion mobility spectrometry (IMS). This approach is a simplified analytical approach as it eliminates need for a high-resolution separation step and substitutes IMS for MS as the detection technology.

Molecular Imprinting of Metal β-Diketonate Polymers

Molecular imprinting can also be used to prepare molecularly imprinted polymers (MIPs) containing β-diketonate polymers for various uses and applications. In this approach, a preselected metal β-diketonate polymer is polymerized in the presence of a chemical template that provides proper spatial and/or geometric orientation for selective capture of a desired analyte (e.g., an explosive, or CW agent). The template can consist of the analyte of interest, a stable or non-toxic surrogate, a structurally similar analogue, or a structurally related compound. Following polymerization, the template is removed, resulting in a polymer with specific cavities that define three-dimensional binding sites that provide the desired selectivity and affinity for an analyte or analytes of interest. However, molecularly imprinted polymers specific toward explosives are difficult to synthesize using traditional free radical polymerization techniques known in the art because nitro groups in the explosives used as the chemical templates scavenge free radicals and interfere with efficient polymerization. In addition, conventional imprinting employs reactive intermediates and elevated temperatures that can degrade sensitive template molecules during the imprinting process. However, making MIPs according to the metal β-diketonate approach is not expected to suffer from traditional templating problems because polymerization and associated cross-linking does not depend on free radical propagation reactions that can be disrupted by the presence of an explosive. Rather, cross-linking is determined by metal coordination in the selected metal β-diketonate polymer, a process that is not expected to be influenced by the presence of a templated explosive. In addition, imprinting using the metal β-diketonate polymerization approach is advantageous since the polymerization conditions are very mild, which promotes stability of the template. Thus, this technique can produce explosive-specific, and other agent-specific MIPs. Specific selectivity for a single analyte is also envisioned using this approach.

Preparation of Capillary Columns that Include β-Diketonate Polymer Stationary Phases Preparation of capillary columns containing metal β-diketonate polymers as stationary phases using an exemplary static coating process will now be described.

Static Coating

General

Static coating deposits a stationary phase film containing a selected metal β-diketonate polymer on the interior of the capillary column by evaporation of a solvent. The blank column is filled with a dilute filtered and degassed solution containing the stationary phase polymer dissolved in a solvent, one end of the column is then plugged, and the column is then immersed in a constant temperature bath (30.0±0.5° C.). Vacuum (typically 20 mTorr) is applied to the capillary at the open end where solvent evaporates or distills slowly from the capillary column, leaving a thin uniform stationary phase film comprising the non-volatile polymer deposited on the capillary wall. The column coating process can be observed by carefully watching the solvent meniscus move through the submerged column as the solvent evaporates. Column coating is complete when the meniscus reaches the far-end column plug. Advantages of this method are that the entire quantity of polymer is deposited on the wall, which allows accurate phase-thickness determination and the technique also results in a uniform stationary phase coating. Because columns of the invention are preferably short, they can be coated within a day. As will be understood by those of ordinary skill in the art, dimensions of capillary columns of the invention are not limited. Thicknesses of coated metal β-diketonate polymers as stationary phases are also not limited. Coating thicknesses for capillary columns will depend at least in part on the inner diameter (I.D.) of the column. For example, phase thicknesses, e.g., for 250 μm I.D. columns can have phase thicknesses that range preferably from about 0.10 μm to 1.0 μm. Larger-bore capillaries (e.g., 320 μm and 530 μm ID) can have typical phase thicknesses of up to about 3.0 μm. Further, capillary columns can have lengths that range from about 1 meter to about 100 meters; typical commercially available lengths range from about 15 meters to 60 meters. Dimensions of multicapillary columns (MCC) are also not limited. Multicapillary columns (MCC) coated with metal β-diketonate polymers for selective capture of explosives can also be prepared with short lengths of from about 1 cm to about 3 cm. Short-length columns can be prepared by coating longer columns and then cutting segments of a desired length. Again, no limitations are intended.

Metal β-diketonate polymers are insoluble in most solvents. For example, lanthanide-(dihed) polymers are insoluble in most solvents other than methanol. However, methanol by itself is not suitable as a solvent for static coating due to its high boiling point (64.7° C.). A coating solution is required that contains methanol solvent for dissolution of metal β-diketonate polymers and that is compatible with 0.4% (w/v) SE-30® solubility. Both of these requirements need to be met while maintaining as low a boiling point as possible to facilitate solvent removal during static coating. To address these requirements, a new azeotrope mixture was tested. Azeotropes are liquids with a boiling point lower or higher than the boiling points of individual constituents in the liquid that also have the capacity to distill without a change in composition. High purity solvents, i.e., methylene chloride (BP=39.8° C.) (Sigma-Aldrich, St. Louis, Mo., USA) and methanol (BP=64.7° C.) (Burdick & Jackson, Muskegon, Mich., USA) form an exemplary binary azeotrope when combined in a precise ratio of 92.7:7.3 (w/w). At this ratio, the binary azeotrope: 1) provides dissolution of SE-30®; 2) provides sufficient lanthanide (dihed) polymer solubility; 3) provides a lower boiling point (BP=37.8° C.) than either pure component; and 4) is compatible with static coating. Other methanol-containing binary, ternary, or higher-order azeotropic mixtures can be used provided they meet solubility and low boiling point requirements.

Evaluation of Custom Capillary Columns

Due to the number of solvents and constituents in the coating solutions, lanthanide-(dihed) polymer solubility (described further herein) is preferably determined experimentally in conjunction with, e.g., ICP/MS analysis. Experimental capillary columns were prepared by simultaneously co-depositing a selected metal β-diketonate polymer and a nonpolar stationary phase polymer (e.g., SE-30®) on the capillary surface. An exemplary stationary phase comprised of lanthanide-(dihed) polymer and SE-30® were co-deposited on the interior capillary surface using a low-boiling azeotrope that offered adequate solubility for lanthanide(dihed) polymer and the SE-30®. This approach was pursued because coating lanthanide(dihed) polymers presently requires a methanol-containing solution to achieve dissolution of the metal β-diketonate polymer. The control SE-30® column was coated from the methylene chloride/methanol azeotrope. Column blanks were 15 m×250 μm I.D. fused silica with a nonpolar surface deactivation. The column blank was coated with the SE-30® polymer solution (0.4% w/v) from the azeotrope, resulting in a film thickness of 0.25 μm. Experimental columns used a lanthanide(dihed) concentration of ~0.05M, determined as follows. The repeating unit molecular weight for La(dihed) of 967 g/mole assumed a polymer composition of $[La_2(dihed)_3]_n$. From these values, 10 mg of La(dihed)/50 mL of 0.4% SE-30® in the azeotrope gave a calculated concentration of 0.05M. Initial experiments demonstrated that the azeotrope dissolved adequate quantities of La(dihed).

To evaluate feasibility of using the methylene chloride/methanol azeotrope for coating, efficiency of an SE-30® control column prepared using the binary azeotrope was compared to commercially available columns (e.g., Quadrex 007-1 and Zebron ZB-1) that contained a cross-linked, non-polar poly(dimethylsiloxane) stationary phase (PDMS). Temperature programmed retention indices were determined by co-injecting a test mixture (i.e., probe) containing explosives-related compounds and/or explosives surrogates with n-alkanes into the columns coated with metal β-diketonate polymers. Column efficiencies of the experimental columns were determined using the isothermal retention time and peak width-at-half-height of n-$C_{14}$. All chromatographic evaluations were performed at a linear helium velocity of 20.0 cm/min as determined by methane retention at 35° C. All injections were split (split ratio of 50:1). Detection of the separated components was by flame ionization detection (FID). TABLE 5 (bottom row) compares chromatographic efficiencies for the custom-coated SE-30® column to conventional Quadrex (007-1) and Zebron (ZB-1) capillary columns used as controls.

TABLE 5

Temperature programmed retention indices for explosives and related compounds on a custom-coated SE-30 ® column prepared from an exemplary azeotropic mixture compared with Quadrex 007-1 and Zebron ZB-1 controls.

| Compound | [a]SE-30 ® (custom-coated) | [b]Quadrex 007-1 | [c]Zebron ZB-1 |
|---|---|---|---|
| 1-Nitrobutane | 804 | 805 | 805 |
| Cyclohexanone | 854 | 867 | 858 |
| n-Pentyl nitrate | 900 | 902 | 901 |
| DMDNB | 1128 | 1154 | 1126 |
| 4-Nitrotoluene | 1170 | 1195 | 1167 |
| 2,6-DNT | 1301 | 1415 | 1385 |
| 2,4-DNT | 1462 | 1498 | 1456 |
| TNT | 1620 | 1648 | 1610 |
| Column Efficiency: (Plates/Meter) | 2700 | 3900 | 4300 |

[a]15 m × 250 μm, $d_f$ = 0.25 μm.
[b]30 m × 250 μm, $d_f$ = 1.0 μm.
[c]30 m × 250 μm, $d_f$ = 0.10 μm.

Retention indices of the explosives-related test probe compounds on the custom SE-30® column were similar on the different columns, although retention of DMDNB; 4-nitrotoluene, 2,6-DNT, 2,4-DNT, and TNT were lower on the custom SE-30® control column compared to the Quadrex column. The retention index for 2,6-DNT was lower on the custom control compared to the Zebron column. Differences in results are attributed to chemistry differences (e.g., different silica deactivations, crosslinking, and choice of PDMS polymers) in the Quadrex and Zebron phase columns compared to the custom column, as well as the different column phase ratios. Efficiency of the SE-300 column was 2700 plates/meter, based on elution of n-$C_{14}$ at 100° C., which was lower than the 3900 or 4300 plates/meter reported for Quadrex 007-1 (n-$C_{12}$ at 120° C. isothermal) or Zebron (n-$C_{14}$ at 100° C.) columns, respectively. However, the SE-30® control is reasonably efficient and suitable for analytical work. Results are significant in that reasonably efficient columns can be prepared using static coating from an azeotropic mixture. This novel approach for coating columns has not been previously described.

Preparation of Columns with Statically-Coated Lanthanide(Dihed) Polymers

Statically coated columns were prepared with various metal β-diketonate polymers from the azeotrope/SE-30® solution and compared with the custom SE-30® column as a control. In the first step in this process, lanthanide-(dihed) polymer coating solutions were prepared. To arrive at a starting concentration for lanthanide(dihed) in the coating solution, a molecular weight corresponding to the polymer repeating unit was calculated assuming a polymer composition of [lanthanide$_2$(dihed)$_3$]$_n$. La(dihed) polymer, for example, has a repeating unit that contains one La(III) cation and 1.5 dihed molecules (MW=967 g/mole). In initial tests, an exemplary concentration of 0.05 M La(dihed) polymer (repeating unit in SE-30®) was used, but is not limited thereto. Columns coated with high (~0.05M) and low (0.025M) concentrations of La(dihed) were designated La(dihed)#1 and La(dihed)#2, respectively. Lower lanthanide-(dihed) coating solution concentrations were also examined for coating Tb- and Eu-containing columns. Chromatographic behavior is related to solubility of the lanthanide(dihed) polymers in the coating solutions. TABLE 6 lists lanthanide concentrations in the coating solutions, as determined by ICP/MS.

TABLE 6

Concentration of lanthanide-(dihed) polymers in the coating solutions, as determined by ICP/MS analysis.

| Polymer | Concentrations | | | |
|---|---|---|---|---|
| | La(dihed)#1 | La(dihed)#2 | Tb(dihed) | Eu(dihed) |
| Coating Solution concentration of Lanthanide Ion (mg/L) | 18.1 | 7.65 | 1.79 | 3.45 |
| Concentration of Polymer repeating unit in SE-30 ® (mM) | 32.6 | 13.8 | 2.82 | 5.68 |

Temperature programmed retention indices were determined by co-injecting a test mixture containing selected explosives-related compounds (i.e., probes) that also contained n-alkanes, as described previously herein. Compounds in the test mixtures included: 1) 1-nitrobutane; 2) cyclohexanone; 3) n-pentyl nitrate; 4) DMDNB; 5) 4-NT; 6) 2,6-DNT; 7) 2,4-DNT; and 8) TNT. Cyclohexanone was included in the test mixture because it is a volatile component associated with RDX compositions and, therefore, has forensic value. This cyclic ketone was also included because it is a much stronger Lewis base than nitroalkanes, nitroaromatics, or nitrate esters (used as probes) in the test mixtures. Retention indices were determined as an indication of each column's selectivity by bracketing the test mixture probes between n-alkanes. A [50:1] split injection was used. Chromatographic tests were performed at a linear helium velocity of 20.0 cm/sec as determined by methane retention at 35° C. A temperature program was used to: ramp column temperature from 35° C. to 185° C. at 4° C./min, but ramp temperatures and rates are not limited. Final temperature was maintained for 15 min. Detection of the separated components was by flame ionization detection (FID).

Figure 11:
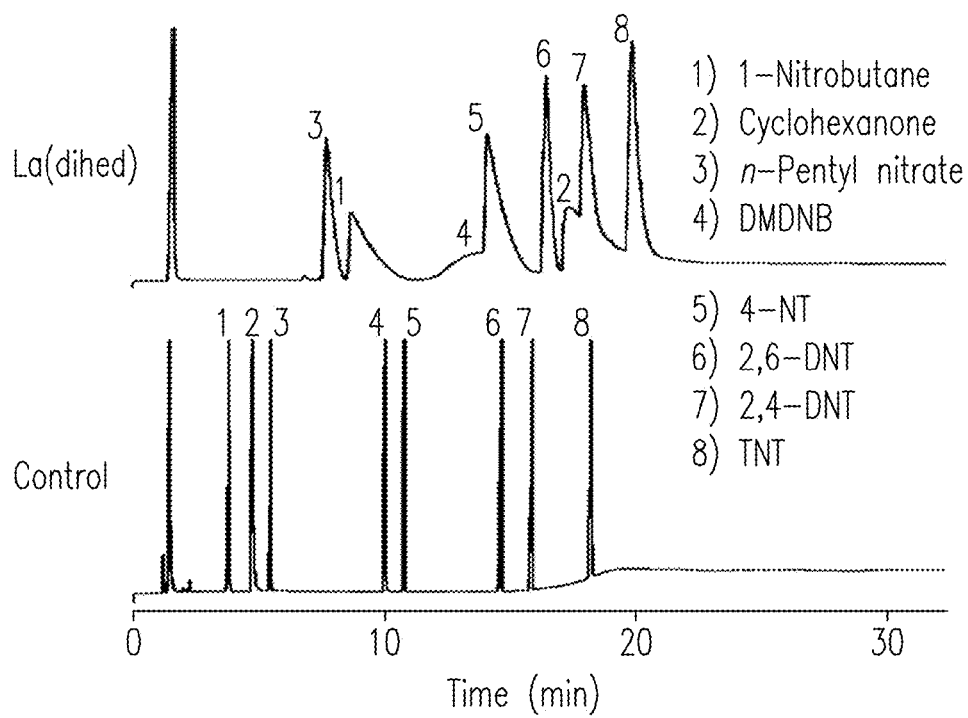
FIG. 11 compares chromatograms of an explosives-related test mixture on a capillary column coated with a high concentration of La(dihed) in SE-30® and a control column coated with SE-30®.
Figure 12:
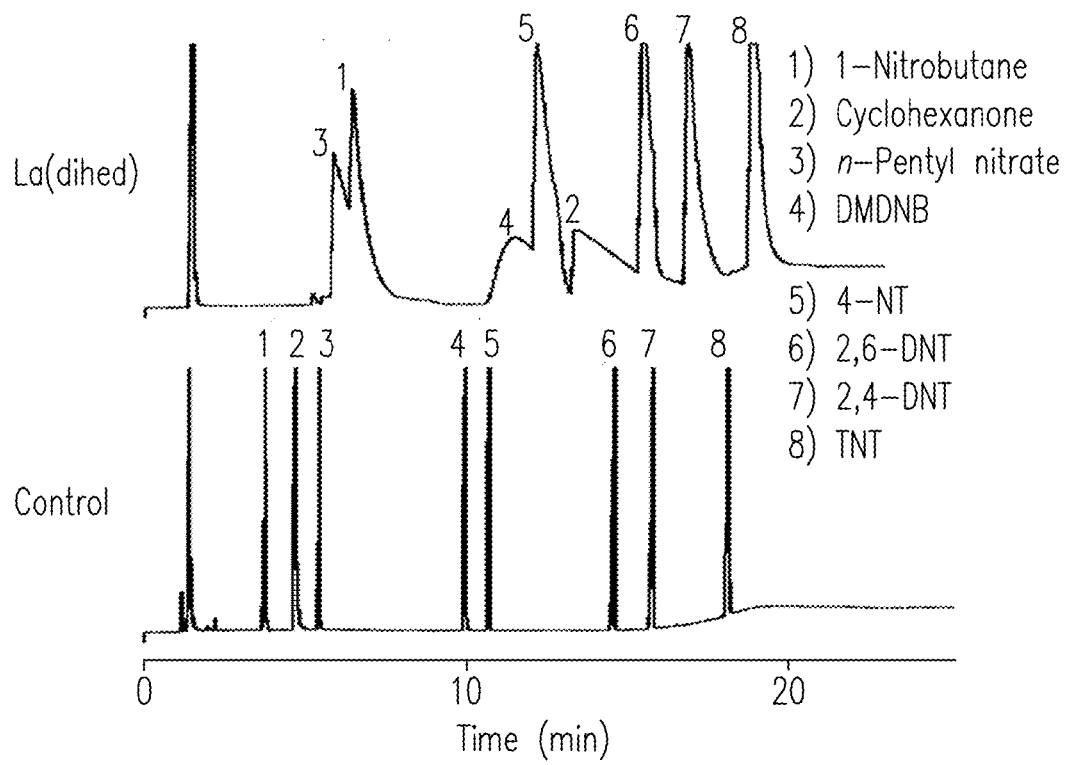
FIG. 12 compares chromatograms of an explosives-related test mixture on a capillary column coated with a lower concentration of La(dihed) in SE-30® and a control column coated with SE-30®.
Figure 13:
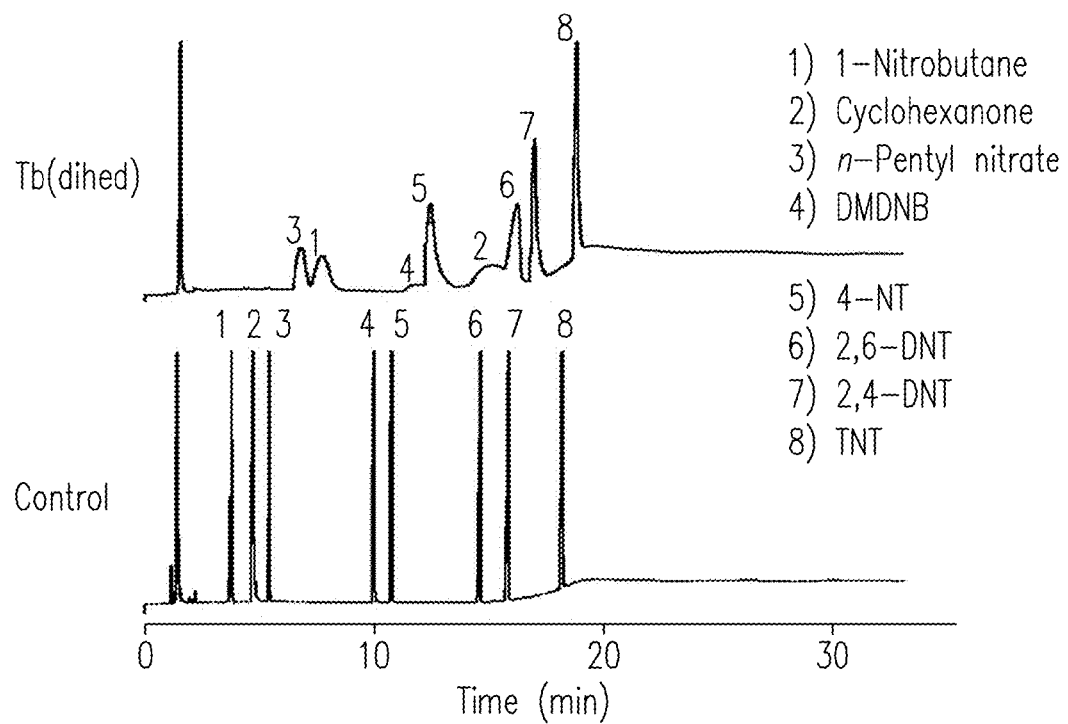
FIG. 13 compares chromatograms of an explosives-related test mixture on a capillary column coated with Tb(dihed) and a control column coated with SE-30®.
Figure 14:
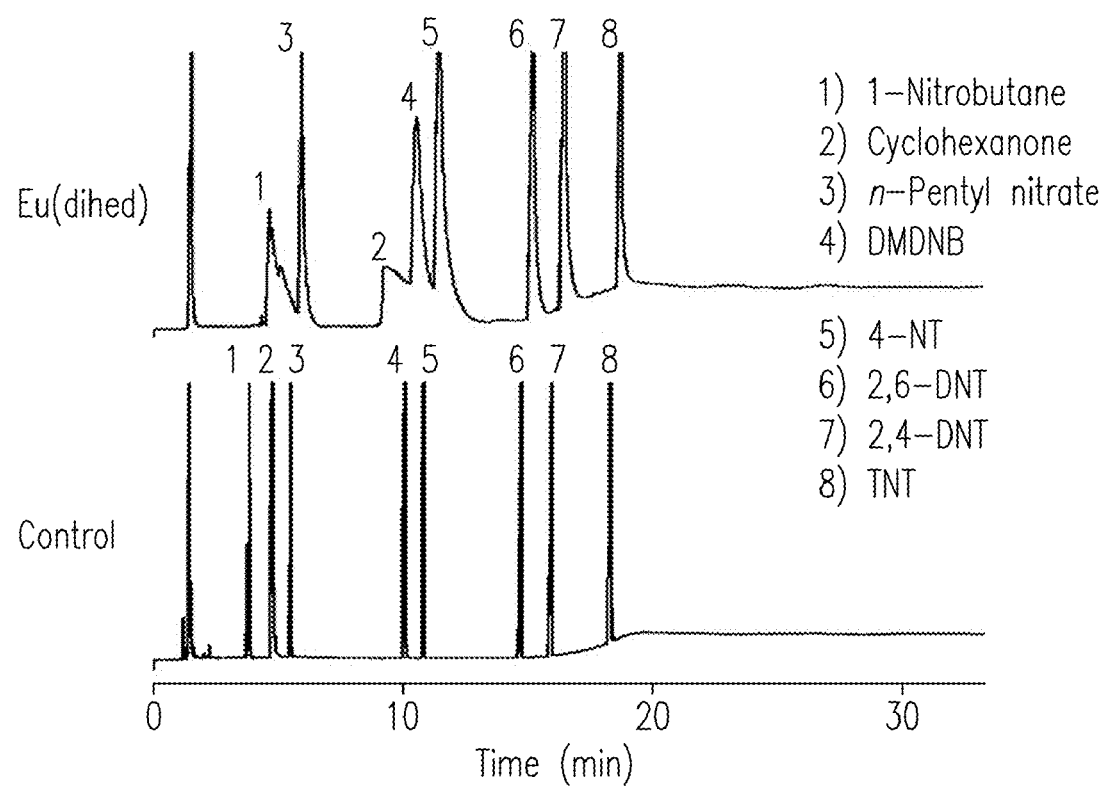
FIG. 14 compares chromatograms of an explosives-related test mixture on a capillary column coated with Eu(dihed) and a control column coated with SE-30®.

FIG. 11 compares chromatograms for an explosives-related test probe mixture separated on a capillary column coated with a high concentration of La(dihed) in SE-30® [La(dihed)#1], and an identical column coated with SE-30® (control). FIG. 12 compares chromatograms for the same explosives-related test mixture separated on a capillary column coated with a lower concentration of La(dihed) in SE-30® [La(dihed)#2], and a column coated with SE-30® (control) under identical conditions. FIG. 13 compares chromatograms for an identical explosives-related test mixture on a capillary column statically coated with Tb(dihed) in SE-30® and an identical column coated with SE-30® as a control. FIG. 14 compares chromatograms for an identical explosives-related test mixture on a capillary column statically coated with Eu(dihed) in SE-30® and an identical column coated with SE-30® under identical conditions. As shown in these figures, the La(dihed)#1 column gave the strongest preferential analyte retention of all the columns. Retention was particularly strong for cyclohexanone. Since metal β-diketonate polymers are Lewis acidic polymers, the stronger base (cyclohexanone) is expected to be most strongly retained. Although the La(dihed)#1 column displayed the strongest retention, this column also had the lowest separation efficiency of any experimental column, a result attributed to the amount of lanthanide-containing polymer in the stationary phase. La(dihed)#2 column gave less overall retention for the test probes, a result expected given the lower concentration of La(dihed) used. Selective retention for the test probes offered by La(dihed)#2 and Tb(dihed) columns was roughly equivalent. Eu(dihed) columns offered even less selective retention and higher separation efficiencies, but offered an improved peak shape for DMDNB over that observed on the La(dihed) columns. Column efficiencies of the experimental columns were determined from the isothermal retention time and peak width-at-half-height of n-$C_{14}$ as described previously herein for the custom SE-30® column. TABLE 7 compares temperature programmed retention indices and column efficiencies for the custom-coated metal β-diketonate polymer columns to the SE-30® coated control.

TABLE 7

Temperature programmed retention indices for experimental lanthanide(dihed) columns compared to an SE-30 ® control.

| Compound | Control | $^a$La(dihed)#1 | $^b$La(dihed)#2 | Tb(dihed) | Eu(dihed) |
|---|---|---|---|---|---|
| 1-Nitrobutane | 804 | 1064 | 1013 | 1002 | 900 |
| Cyclohexanone | 854 | 1531 | 1391 | 1399 | 1183 |
| n-Pentyl nitrate | 900 | 1005 | 949 | 955 | 931 |
| DMDNB | 1128 | 1331 | 1234 | 1221 | 1219 |
| 4-Nitrotoluene | 1170 | 1331 | 1271 | 1233 | 1227 |
| 2,6-DNT | 1301 | 1524 | 1439 | 1465 | 1416 |
| 2,4-DNT | 1462 | 1616 | 1537 | 1520 | 1494 |
| TNT | 1620 | 1714 | 1650 | 1641 | 1629 |
| TATP | 1094 | 1046 | --- | 1094 | 1092 |
| NG | 1299 | 1332 | --- | 1303 | 1301 |
| Column Efficiency (plates/meter) | 2700 | 230 | 1000 | 2200 | 2600 |

$^a$10 mg La(dihed)/50 mL azeotrope solution containing SE-30 ®.
$^b$5 mg La(dihed)/50 mL azeotrope solution containing SE-30 ®.

Figure 15:
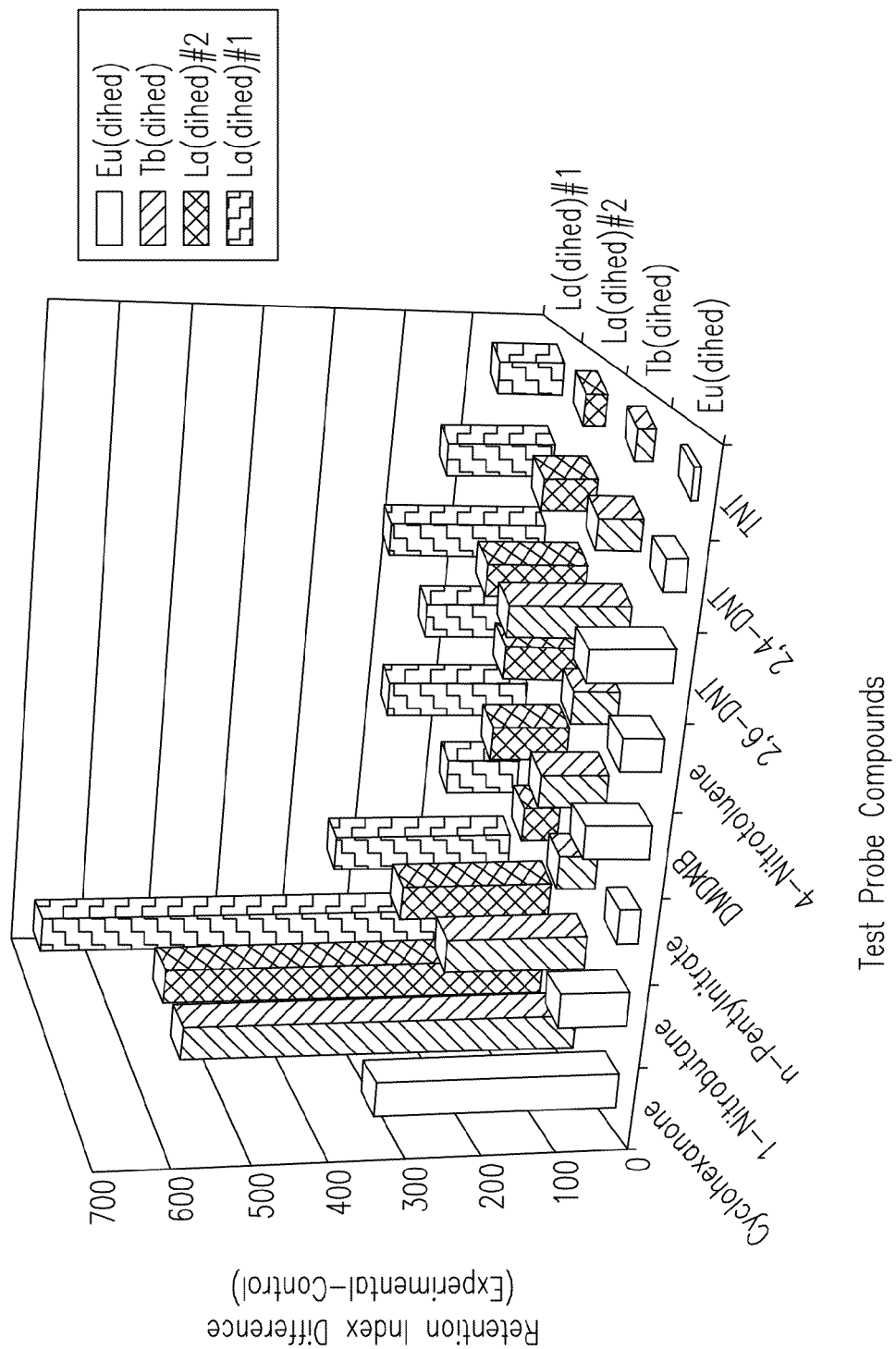
FIG. 15 shows changes in retention index values observed on metal (dihed) columns relative to a control column.

In the table, a metric for the magnitude of the selective interaction of a test compound with a metal β-diketonate polymer can be obtained by subtracting the retention index for a test probe on a given column from the index for the same compound on the control column. Column efficiencies of the lanthanide(dihed) columns were 230, 1000, 2200, and 2600 plates/meter for La(dihed)#1, La(dihed)#2, Tb(dihed), and Eu(dihed) columns, respectively, which were less than the SE-30® control efficiency of 2700 plates/meter. A reduced injection temperature was used (e.g., 185° C.) to analyze the thermally labile explosives TATP and NG, as described previously. Sharp peaks were observed on the SE-30® control column for TATP and NG with temperature programmed retention indices of 1094 and 1299, respectively. NG gave nearly identical retention indices as the control on Eu(dihed) (i.e., 1301) and Tb(dihed) (i.e., 1303) columns, a result that indicates the absence of selective retention relative to the control. The most retentive column, La(dihed)#1 gave moderate selective retention of NG as indicated by the retention index of 1332. For TATP, retention indices of 1092 and 1094 for Eu(dihed) and Tb(dihed) columns were essentially the same as the control column which again indicates the lack of enhanced retention over the control. TATP gave a reasonably sharp peak with a lower retention index (1046) on the La(dihed)#1 column compared to the control (1094). Results suggest TATP is catalytically transformed to another stable product during analysis on the La(dihed)#1 column. In the table, the largest retention increase and most selective retention was for cyclohexanone, a stronger Lewis base than other probes in the test mixture. The La(dihed)#1 column gave the most preferential and strongest retention. La(dihed)#2 and Tb(dihed) columns gave roughly similar increases in retention compared to the control. The Eu(dihed) column gave the least selective retention for most test probes. While the greater retention exhibited by La(dihed)#1 column over La(dihed)#2 column was expected due to a greater polymer concentration in the coating solution, the general overall compound, selectivity of La(dihed)#1>La(dihed)#2≈Tb(dihed)>Eu(dihed) is seemingly contrary to the Lewis acidity of metal cations [Tb(III)>Eu(III)>La(III)]. The observed selectivity is due to a higher solubility of La(dihed) in the coating solution compared to other lanthanide(dihed) polymers. FIG. 15 shows changes in retention index values observed for the eight probe tests conducted on the four lanthanide(dihed) columns relative to the control. In the figure, La(dihed)#1 gave the most preferential retention of the test probe compounds, La(dihed)#2 and Tb(dihed) columns gave roughly similar intermediate retention over the control, whereas Eu(dihed) gave the least selective retention for the test probes.

In sum, experimental columns prepared using the static coating process demonstrate enhanced retention, unique selectivity, and a range of selective retention capabilities compared to control columns, based on the selected (dihed) polymer used in the stationary phase and the Lewis basicity of the analyte of interest. Although Tb(III) and Eu(III) are stronger Lewis acids than La(III), results show that the lower concentrations used results in an overall lower retention than for the lanthanide (dihed) columns. Tb(dihed) and La(dihed) polymers are also highly luminescent and when incorporated in a stationary phase are expected to provide superior properties for sensitive and selective on-column chromatographic detection based on changes in polymer luminescence, e.g., as separated analyte bands transverse a detection window.

Selective Sampling with Direct Ion Mobility Spectrometric Detection for Analysis of Explosives Direct coupling of a sampling/preconcentration stage in conjunction with metal β-diketonate-containing fibers, filters, and/or stationary phase cartridges or columns in combination with, e.g., ion mobility spectrometry (IMS) detection represents an instrument configuration with important remote field applications. A major advantage is the ability to perform analyses entirely in the field, e.g., using handheld, field-deployable instrument formats. For example, sample collection/concentration using selective SPME concentration on metal β-diketonate-containing fibers with, e.g., laboratory-based IMS analysis is expected to be sufficiently selective to allow simplification of analysis/detection for radically streamlined analysis approaches described herein. For example, the invention employed in various combination instrument configurations and approaches can eliminate need for a high resolution, capillary GC separation step and further can substitute a simple, compact, and lightweight ion mobility spectrometer (IMS) for MS detection. The approach may not be as powerful as, e.g., SPME/GC/MS/SIM methods due to a lack of chromatographic separation and limited mass discrimination capability of IMS. In addition, some matrix interferences and analytical artifacts can occur in the absence of a separation stage that can complicate sample analysis. A simplified analytical approach will now be described that was used to evaluate selective sample capture on deactivated quartz fiber filters impregnated with metal β-diketonate polymers in combination with direct desorption of compounds, for IMS detection.

Uptake of (TNT) and (RDX) Explosives on Metal β-Diketonate-Impregnated Quartz Fibers Deactivated quartz fiber filters impregnated with metal (dihed) polymers [e.g., Zn(dihed), Eu(dihed), and La(dihed)] were directly inserted into an IMS instrument for analysis. Background tests of these filters with IMS gave ion mobility spectra that contained an artifact peak at a drift time of 16.2 ms that is attributed to a hydrolysis product of the $H_2$(dihed) ligand, i.e., [p-(4,4,5,5,6,6,6-heptafluorodionyl)acetylbenzene] which complicates detection of explosives due to competitive ionization. Cu(dihed) impregnated filters do not show the artifact. Muslin cloth, a typical filter material used in airport screening tests and IMS swipe tests, gave IMS backgrounds that were slightly higher than those of the Cu(dihed) impregnated quartz filters. The Cu(dihed) filters give a slightly higher background in the explosives drift region. Cu(dihed) filters were then spiked with TNT (15 ng) and RDX (15 ng) standards. Explosives 2,4,6-trinitrotoluene (TNT) and hexahydro-1,3,5-trinitro-1,3,5-triazine (RDX) were purchased (Hercules, Wilmington, Del., U.S.A.) and purified by repetitive recrystallization from ethanol or acetone, respectively, prior to use. Tests showed detection limits of ~1 ng for either explosive, a value comparable to detection limits attainable on industry-standard muslin cloth. 2,4,6-trinitrotoluene (TNT) gave an expected ion (i.e., $TNT^-$) that matches a reduced mobility ($K_0$) of 1.45 $cm^2V^{-1}s^{-1}$ reported in the literature. RDX gave 2 expected ion clusters (i.e., $RDX \cdot NO_3^-$ and $RDX \cdot Cl^-$) that match with reduced mobility values reported in the literature: $K_0 = 1.31$ $cm^2V^{-1}s^{-1}$ and $K_0 = 1.39$ $cm^2V^{-1}s^{-1}$, respectively.

In other experiments, uptake kinetics of TNT were characterized. First, TNT uptake from a TNT saturation jar showed both the control and Cu(dihed) filters reached equilibrium at approximately 24 hr, with the Cu(dihed) filters displaying an additional ~60% enhanced uptake compared to quartz fiber controls. This differential uptake is significant given the low 1.5% (w/w) loading of the selected polymer on the filter. Longer pre-equilibrium sampling periods showed increased quantities of TNT captured, indicating that TNT capture in the saturation chamber results from gas-phase adsorption, not from dusting by TNT particulates. Capture of TNT particulates is indicated by large variability in TNT quantities. Duplicate TNT uptake values agreed within a narrow range, which is consistent with gas-phase capture rather than particulate dusting. Next, Cu(dihed)-impregnated filters were used for passive-equilibrium sampling of air in an ammunition magazine that contained TNT. A 48-hr collection period was used, but is not limited thereto. This analysis gave an order of magnitude estimate for vapor-phase concentration of TNT of 0.264 ppbv.

Figure 16A:
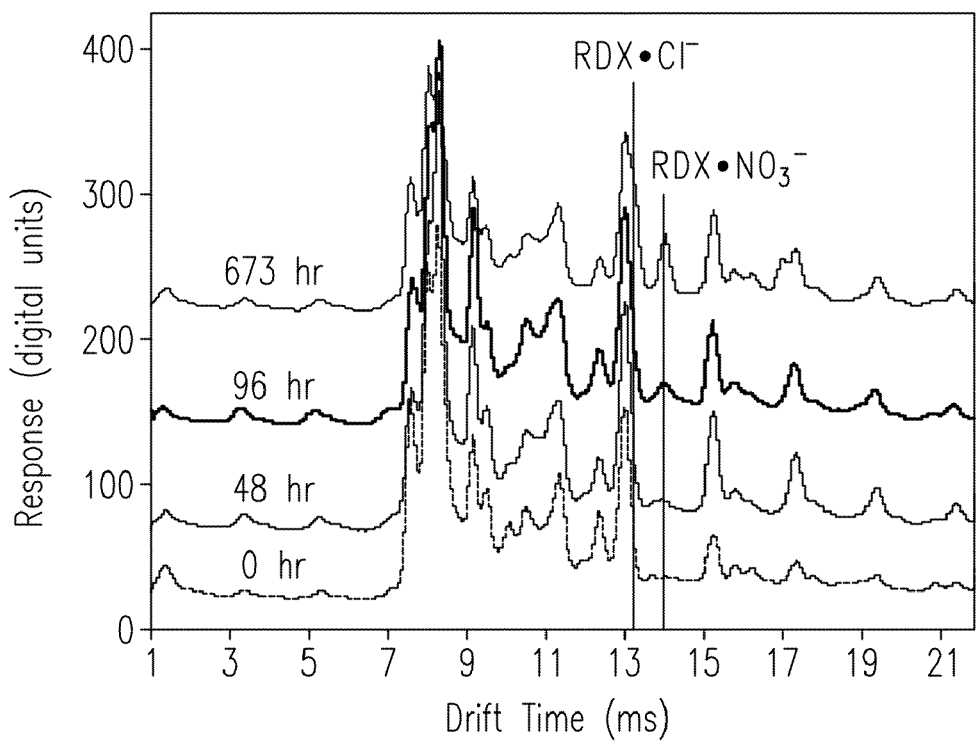
FIGS. 16a-16b show ion mobility spectra for uptake of RDX explosive from a saturated environment on a Cu(dihed)-impregnated filter.
Figure 16B:
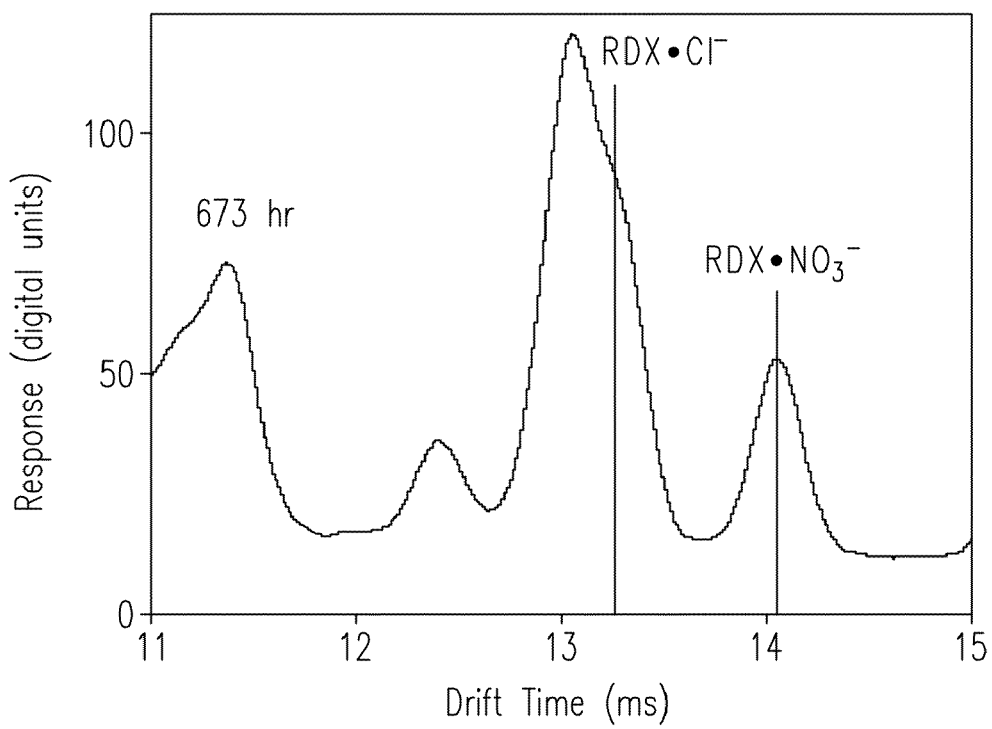

In other experiments, uptake kinetics of hexahydro-1,3,5-trinitro-1,3,5-triazine (RDX) from a saturated environment was assessed. FIG. 16a shows IMS ion mobility spectra for RDX uptake from a saturated environment (atmosphere) at 0 hrs, 48 hrs, 96 hrs, and 673 hrs, respectively. In the figure, uptake of RDX from the saturated environment increases for each incremental sampling period as evidenced by the increased signal intensity for the RDX nitrate ion cluster ($RDX \cdot NO_3^-$). Appearance of the RDX chloride ion cluster ($RDX \cdot Cl^-$) further verifies the presence of RDX. The steady increase in RDX nitrate ion cluster intensity in the negative ion mobility spectra with increasing sampling times verifies the gas-phase uptake, not capture of particulates, on the filter. Comparison to an RDX standard indicated ~5 ng of RDX was collected on the filter at the end of one month exposure. FIG. 16b shows an enlargement of the 11 ms to 15 ms region of the ion mobility spectrum for the 673 hr uptake period. RDX chloride ion cluster appears as a shoulder to the right side of the Cu(dihed) artifact peak at 13.05 ms. Preliminary tests demonstrate gas-phase uptake of RDX, a low-volatility explosive, under saturated conditions for the first time.

Further improvements in approaches described herein can be expected by implementing active sampling. In active sampling, air is actively drawn through the collection filter. Preliminary attempts at this approach were not successful due to artifact formation (presumably a ligand hydrolysis product) that interfered with IMS detection (competitive ionization). These active sampling studies are described in more detail in EXAMPLE 12. Further improvements can therefore be achieved by minimizing artifact formation using metal β-diketonate polymers that contain a non-fluorinated ligand [e.g., $H_2$(ppb) or $H_2$(pbb)] since such ligands are less susceptible to hydrolysis. Lower detection limits will be achieved if polymer hydrolysis during active sampling can be minimized. Additional analytical improvements can be expected in conjunction with use of new fast GC/MS instruments (e.g, GUARDIAN-7™ suitcase GC/MS, Torion Technologies, Inc., American Fork, Utah) in exchange of IMS. The following Examples provide a further understanding of the invention.

Example 1

Preparation of Coated SPME Fibers

Two groups of SPME fibers were examined, a group that was coated with 7-μm poly(dimethylsiloxane) (PDMS) and one coated with 30-μm PDMS. One fiber within each group was further dip-coated in a concentrated solution (~250 mg/mL) of La(dihed) dissolved in methanol. Methanol was removed by evaporation, leaving a coating of the selected metal β-diketonate polymer deposited over the top of the PDMS-coated fiber. PDMS fibers not coated with metal β-diketonate polymer served as controls.

Example 2

Preparation of Metal β-Diketonate Polymer Stationary Phases

Stationary phase mixtures were prepared from a mixture of metal β-diketonate polymers dissolved or suspended in methanol and deposited onto a control material, described further hereinbelow. Methanol solvent was removed by rotary evaporation, resulting in a 5% (w/w) loading of metal β-diketonate polymer on the control support material. The control support material was prepared from an inert, deactivated diatomaceous earth, e.g., CHROMQSORB-W® HP (100/120 mesh) (Supelco, Bellefonte, Pa., USA), which was further loaded with 3% (w/w) of a poly(dimethylsiloxane) elastomer (e.g., SE-30® polymer, Supelco, Bellefonte, Pa., USA) prepared in methylene chloride solvent. Methylene chloride was removed by rotary evaporation. The control support material was used either alone (control stationary phase) or further loaded with metal β-diketonate polymers to form the experimental stationary phases for packed-column GC studies, as described hereinabove. These column packing materials can also serve as selective air sampling sorbents.

Example 3

Sorbent-Packed Chromatographic Columns Comprising Metal β-Diketonate Polymers

Control sorbents were prepared with a 3% loading (w/w) of SE-30® polymer (Supelco, Bellefonte, Pa., USA) coated onto a support material comprised of CHROMOSORB-W® HP (100/120 mesh) (Supelco, Bellefonte, Pa., USA). Experimental sorbents were prepared by coating a 5% (w/w) loading of a selected metal β-diketonate polymer from methanol onto the control sorbent, as described in EXAMPLE 2. Sorbents (experimental or control) were packed into column blanks made from stainless steel tubing cut to an appropriate length. End plugs were made from silanized glass wool. A first column had exemplary column dimensions of 8 ft.×⅛ in. O.D. The I.D. of the column was 0.083 in. (2.1 mm). A second column had exemplary column dimensions of 2 ft.×⅛ in. O.D. The I.D. of the column was 0.083 in. (2.1 mm). Dimensions are not limited.

Example 4

Gas Chromatographic Analyses of Analytes on Packed Columns

A Hewlett-Packard 5890 Series II gas chromatograph, modified with a packed column conversion kit was used. Helium carrier gas was delivered to the column at a flow rate of 25 mL/min through an injection port maintained at 200° C. Septum purge was adjusted to 1.5 mL/min. Columns were conditioned with helium flow at 210° C. overnight before connecting to the flame ionization detector. The detector temperature was held at 250° C. Sample injections were typically 1-2 μL of pentane or methylene chloride solvent that contained analytes of interest. Analyses were performed at various isothermal temperatures, or one of two temperature programs. Temperature programs started at 50° C. for 2 min before ramping at 10° C./min to a final temperature of either 180° C. or 200° C.; the final temperature was maintained for the remainder of the chromatographic run. Chromatographic traces were recorded on a Hewlett-Packard Model 3395 integrating recorder. The same gas chromatograph without the conversion kit was used for evaluation of capillary columns.

Example 5

Kováts Indices

Retention and Selectivity Assessment of Chromatographic Columns with Metal β-Diketonate Polymers Kováts indices were calculated from retention data (collected in triplicate) on both experimental and control columns for analytes introduced at defined temperatures. Data used to calculate Kováts indices were collected at 200° C. by bracketing TNT between n-alkanes on the control and metal β-diketonate columns. Adjusted retention times were calculated by using methane as a dead volume marker.

Example 6

Collection of Organic Matrix Backgrounds from Air Samples

Organics from a large-volume air sample were collected on a 60 g bed of XAD-2, a porous poly(styrene-divinylbenzene) support (Alltech Associates, Inc., Deerfield, Ill., USA), which was sandwiched between two polyurethane foam plugs. The sorbent bed was exhaustively extracted with a series of solvents and dried in a vacuum oven prior to use. A vented ring compressor was used to pull $10^6$ L of air through the sorbent bed over a 68 hour period. Sorbed organics were subjected to Soxhlet extraction with pentane solvent. The resulting pentane extract was reduced in volume using a stream of dry nitrogen, split into two aliquots, one of which was fortified with TNT. Sample injections introduced to the gas chromatograph corresponded to an extrapolated 200 L of air. The fortified sample contained an extrapolated 47-ppt (v/v) TNT. Samples were analyzed on experimental and control columns prepared as detailed in EXAMPLE 4.

Example 7

Deactivated Quartz Fiber Filters Interfaced to an Ion Mobility Spectrometer (IMS) for Selective, Trace-Level Determination of Selected Explosives Quartz fiber filters (3.2-cm diameter, #1851-032, QMA grade) were obtained from Whatman (purchased through VWR, West Chester, Pa., USA). Deactivation and polymer loading of these filters were performed in an explosives-free laboratory. Filters were deactivated in a solution of dichlorodimethylsilane:methylene chloride (1:9, v/v) followed by two rinses in methylene chloride and three rinses with methanol. Dichorodimethylsilane used for deactivation of quartz fiber filters was procured (Sigma-Aldrich, St. Louis, Mo., USA). Deactivated filters were dried in a vacuum oven overnight at 100° C. under house vacuum (~50 Torr). Polymer-impregnated filters were prepared by applying 100 μL of a methanol solution that contained 1 mg of dissolved [lanthanide(dihed)] or slurried [Cu(dihed)] polymers to a methanol-moistened deactivated filter. Pre-moistening the filter with methanol aided in homogeneous dispersion of the polymers. The polymer-containing filters were again dried in a vacuum oven overnight at 50° C. under reduced pressure. Filters were placed in 60-mL EPA clean jars for storage and transportation. IMS muslin cloth wipes (Smiths Detection, Warren, N.J., USA) were used for comparison to metal β-diketonate-containing filters. A Barringer Ionscan 400A IMS instrument (Smiths Detection) designed for use with muslin cloth wipes was used. Wipes were placed in a sliding stage mount that could be inserted into the instrument for thermal desorption into a purified air stream used as the drift flow gas. The sample interface was compatible with substituting glass fiber filters (3.2-cm diameter) for the muslin wipes. The instrument was operated in the negative-ion mode using hexachloroethane as a dopant gas to control ion chemistry in the drift tube and 4-nitrobenzyl nitrile as a calibrant. Desorption was performed at 175° C. for 10 s, and the transfer tube was held at 185° C. for all experiments. Spectra were collected after a 25 ms delay following desorption using a shutter grid width of 0.2 ms and a scan period of 22 ms. Otherwise, standard analytical conditions, as defined by the Barringer Ionscan software, were used (i.e., 114° C. drift temperature, 240° C. inlet temperature, 351 mL/min drift flow, and 239 mL/min sample flow).

Example 8

Static Coating of GC Capillary Columns

Fused silica capillary columns (15 m×250 µm I.D.) with a nonpolar, deactivated surface were obtained (Part No. 25756, Supelco, Bellefonte, Pa., USA). Coating solutions were prepared from a binary azeotrope consisting of methylene chloride:methanol (92.7:7.3, w/w). Control columns were prepared from a coating solution that contained a PDMS elastomer, SE-30® (Supelco, Bellefonte, Pa., USA) dissolved in the azeotrope at a concentration of 0.4% (w/v). Experimental columns were prepared from a coating solution that contained lanthanide (dihed) polymers added to the azeotrope/SE-30® solution at concentrations of either 5 mg in 50 mL (0.1 mg/mL) or 10 mg in 50 mL (0.2 mg/mL), which was stirred for a minimum of 2 hours. Coating solutions were filtered through 0.5-µm filters (e.g., Millex-LCR filters, Millipore, Bedford, Mass., USA), briefly sonicated to degas the solution, and then used to fill the capillary blank columns. After filling, the capillary column end was plugged by immersing in a vial of Apiezon®-N [CAS No: 8012-95-1] (M&I Materials, Ltd., Manchester, M32 0ZD, UK), a hydrocarbon grease used typically for cryogenic and high vacuum applications. The other column end was removed from the capillary filling apparatus. Static coating was initiated by submerging the column in a water bath held at 30.0±0.5° C. and applying vacuum (~20 mTorr) to the open end. After coating, the column was removed from the bath, ends were trimmed, and the column was purged with helium (He) for several hours, and then thermally conditioned, as described further herein (see EXAMPLE 9). Two La(dihed) columns were prepared: one was coated at the 10-mg La(dihed)/50-mL azeotrope/SE-30® concentration [La(dihed)#1] while the second was coated with a 5-mg La(dihed)/50-mL azeotrope/SE-30® solution [La(dihed)#2]. Eu(dihed) and Tb(dihed) columns were coated from solutions that contained 5 mg of lanthanide(dihed)/50 mL azeotrope/SE-30® solution. Most of the added La(dihed) dissolved in the coating solutions, whereas significant undissolved residue was noted in both the Eu(dihed) and Tb(dihed) solutions. To obtain an accurate concentration of lanthanide(dihed) polymer in the coating solutions, aliquots were diluted 1000-fold in aqueous 1.0% nitric acid and analyzed by ICP/MS (PQ-ExCell Instrument, Thermo Electron Corp., Waltham, Mass., USA). The spray chamber was held at 2° C. during sample introduction. Analyses were performed in semi-quantitative mode, using indium as a surrogate reference standard for the analysis of rare earth elements. This approach typically gives concentration values accurate to within ±20%.

Example 9

Thermal Conditioning and Evaluation of Coated Capillary Columns

A 5890 Series II gas chromatograph (Agilent, Santa Clara, Calif.) with a flame ionization detector was used. The injector was held at 250° C. and the detector at 290° C. for most experiments. Studies that examined TATP and NG used a reduced injector and detector temperature of 185° C. and 250° C., respectively. Standard mixtures were introduced to the column by split injections with a split ratio of 50:1. Chromatograms were recorded on an HP-3395 recorder integrator. Columns were conditioned with helium flow by ramping the oven from 35° C. to 185° C. at a rate of 4° C./min and holding the upper temperature for 2 hours. After thermal conditioning, the linear velocity of helium was adjusted to 20.0 cm/sec by monitoring the retention time of methane at 35° C. Column efficiency was determined by injecting a series of n-alkanes under isothermal conditions at 100° C. Retention time and peak-width-at-half-height of C-14 was used to calculate the number of theoretical plates. Chromatographic runs of the test probes used temperature programs that started at 35° C. and ramped to 185° C. at a rate of either 4° C./min (for determination of retention indices) or 8° C./min (see FIGS. 11-14) with the final temperature being held for 15 min. Retention indices for NG and TATP were determined with a program ramp of 8° C./min. Temperature-programmed retention indices were determined by co-injecting a series of n-alkanes with the test probe mixture. In cases where one of the test probes (i.e., test compounds) co-eluted with one of the alkanes, independent runs of the probe alone, or with a non-interfering alkane, were used to extrapolate a retention index. Quadrex 007-01 (Woodbridge, Conn.) and Zebron ZB-1 (capillary GC) columns (Phenomenex, Torrance, Calif.) were used as reference to compare results for a custom-coated SE-30® column. The Quadrex column was 30 m×250 µm I.D. ($d_f$=1.0 µm). The Zebron column was 15 m×250 µm I.D. ($d_f$=0.10 µm).

Example 10

TNT and RDX Saturation Chambers

The TNT saturation chamber for SPME experiments consisted of a 4.0 mL amber vial with a polytetrafluoroethylene (PTFE)-lined septum screw cap that contained a ~5 mg flake of military-grade TNT (Hercules, Wilmington, Del., USA). For experiments that used deactivated quartz fiber filters, a TNT saturation chamber was constructed by placing several flakes (~5 mg) of military-grade TNT at the bottom of a 60-mL jar and then layering silanized glass wool (Supelco, Bellefonte, Pa., U.S.A.) over the flakes. The Cu(dihed) filter was then placed on top of the glass wool during the sampling period. For RDX, a slight variation that eliminated the use of glass wool was used. This modification was found to be necessary because impurities from the glass wool became concentrated during the longer sampling periods required for RDX. For the modified approach, several crystals of RDX were placed in the bottom of a 4.0-mL vial, and the vial was carefully placed horizontally in the saturation jar. During sampling, a filter was positioned in the jar so it did not contact the vial opening. Vapor pressures for TNT and RDX were calculated from the Clausius-Clapeyron expression, as given by Equation [3], as follows:

$$\text{Log}_{10} P(\text{Torr}) = A - B/T(K) \qquad [3]$$

Here, (A)=14.53 and (B)=5900 for TNT; and (A)=15.12 and (B)=7011 for RDX as reported in the literature [Rosenblatt et al., "Organic Explosives and Related Compounds" in: *The Handbook of Environmental Chemistry, Anthropogenic Compounds*, Vol. 3, Part G, O. Hutzinger (Ed.), Springer-Verlag, Berlin (1991) pp. 195-234]. Saturation concentrations for TNT and RDX were calculated by dividing vapor pressures by the atmospheric pressure. Saturation concentrations calculated with these parameters were 7.08 ppbv and 5.16 pptv for TNT and RDX, respectively.

Example 11

TNT Uptake from a Saturated Environment

SPME sampling consisted of inserting the needle sheath through the septum into the saturation vial, exposing the fiber for a prescribed period, and withdrawing the fiber into the needle sheath before removing from the chamber and analyzing by GC/MS. Uptake of TNT on SPME fibers from the saturation vial was studied for the PDMS control and La(dihed) fibers for uptake periods of up to 96 hrs. It was found that PDMS fibers reached equilibrium at approximately 24 hrs. Once a fiber had reached equilibrium, very little additional uptake was observed with additional exposure. At equilibrium, the amount of TNT on the fiber is directly proportional to the vapor-phase concentration. TNT uptake on the La(dihed) fiber was significantly higher than the PDMS fiber for all sampling periods. La(dihed) showed a linear uptake throughout the 96 hrs indicating that the fiber uptake had not approached equilibrium even after this lengthy exposure, which may be due to diffusion limitations in the glassy polymer. For analysis of TNT collected/concentrated on metal β-diketonate polymer-impregnated filters, TNT was determined from ion signal data generated from IMS analyses of TNT standards [reduced mobility ($K_0$) of 1.45 $cm^2V^{-1}s^{-1}$, with a percent relative standard deviation (% RSD) of 0.1, where n=4 (repeat analyses)] compared to signal data from analysis of collections on Cu(dihed)-impregnated filters. Mobility ($K_0$) values observed for standards agreed with literature values [e.g., Koyuncu et al., *Turk. J. Chem.* (2005) 29:255] and values reported by the IMS instrument manufacturer (e.g., Barringer Ionscan 400A, Smiths Detection, Warren, N.J., USA) (e.g., $K_0$=1.45 $cm^2V^{-1}s^{-1}$). Duplicate values from TNT uptake experiments were in close agreement (i.e., a range deviation from the mean of less than 15 percent). Samples reached equilibrium at approximately 24 hr. Cu(dihed) filters displayed enhanced uptake compared to controls. At 96 hrs, uptake was greater in the Cu(dihed) filters by 64 percent compared to the control. The differential uptake is significant given the low loading of the polymer on the filter (~1.5 percent by weight). That longer sampling periods captured increasing quantities of TNT, along with agreement between duplicate samples, suggests results are from gas-phase capture and not from dusting by TNT particulates in the saturation chamber. Cu(dihed) filters were used only once during the TNT uptake experiments. However, a limited number of trials were conducted with previously used filters. Results show Cu(dihed) filters can be used numerous times without degradation in performance.

Example 12

TNT Sampling in an Explosives Bunker

Sampling was conducted in a CONEX® container (6.10 m×2.44 m×2.44 m) used as an explosives bunker. The bunker contained two ammunition boxes (1.22 m×1.22 m×1.22 m), one contained bulk explosives (500 g TNT, 500 g RDX, and 100 g tetryl) as well as small amounts of 2,4-DNT and nitrate esters. The bulk explosives were loosely wrapped in plastic bags that were enclosed within cardboard boxes, while the 2,4-DNT and nitrate esters were stored in snap-cap containers used for storing neat explosives. Vapor concentrations of TNT in the bunker room air and within the ammunition magazine were determined by SPME experiments (i.e., using PDMS fibers) to be less than 3 pptv and 33 pptv, respectively. Quantification was based on TNT uptake studies (EXAMPLE 11) that indicated SPME fiber equilibrium on PDMS is achieved within 24 hrs. The 48-hr SPME sampling ensured that equilibrium had been reached and the amount of TNT captured on the fiber was directly proportional to the air concentration. Based on these assumptions, the vapor phase concentration of TNT in the bunker and magazine was estimated. Bunker SPME samples [PDMS and La(dihed) fibers] were simultaneously collected from the same environment for a 48-hr period and then analyzed by GC/MS with SIMS detection. Samples for the IMS were collected by either actively pulling bunker room air through the Cu(dihed) filters, or by passively sampling the more concentrated TNT vapors from air within the ammunition magazine. Bunker room air was sampled by pulling either 512 L or 2776 L of air through filter filters at 1 L/min using an air sampling pump. Ion mobility spectra from these samples showed increasing quantities of the artifact component (16.2 ms) with no indication of TNT. It is likely that large-volume air samples contained sufficient moisture to facilitate ligand hydrolysis. As previously noted, the artifact suppresses the TNT signal because of competitive ionization. Further studies used Cu(dihed) filters to passively sample air inside an ammunition magazine environment that previously was determined by SPME experiments to contain TNT at approximately an order of magnitude higher concentration than the room air. Samples were collected for 48 hr to achieve equilibrium before analysis by IMS. A TNT signal that corresponded to approximately 25 ng was observed when these samples were analyzed. Assuming equilibrium has been achieved, the quantity of TNT passively captured on the filters will be directly proportional to the air concentration. Direct comparison of peak areas from filters used to sample the ammunition magazine air to those in equilibrium with saturated TNT vapors, an approximate order-of-magnitude estimate of 0.264 ppbv TNT concentration was obtained for the ammunition magazine air, or about eight times higher than that found during previous SPME studies. This is only an approximate estimate given the experimental limitations, which include possible interferences from other volatile magazine components, integration on the leading edge of the polymer artifact at 12.95 ms, and the limited dynamic range of IMS.

Example 13

RDX Uptake from a Saturated Environment

A series of ion mobility spectra showing RDX uptake on Cu(dihed)-impregnated filters from a saturated environment for sampling periods of up to one month are shown in FIG. 16a. The drift time of the artifact peak appearing at 15.28 ms was consistent in all ion mobility spectra with the exception of the 96-hr collection period where the ion drift time was 0.10 ms lower. To facilitate comparison between ion mobility spectra, a +0.10-ms drift time offset was applied to the 96-hr spectrum. The spectra show an increasing signal intensity for the RDX nitrate ion cluster (labeled as RDX·$NO_3^-$) at increased sampling periods. This ion has a $K_0$ of 1.32 $cm^2V^{-1}s^{-1}$ that agrees well with: 1) the reduced mobility value obtained upon analysis of an RDX standard [i.e., $K_0$=1.32 $cm^2V^{-1}s^{-1}$ with a percent relative standard deviation (% RSD) of 0.02, where n=5 (repeat analyses)], 2) a $K_0$ value of 1.31 $cm^2V^{-1}s^{-1}$ reported in the literature. [e.g., Koyuncu et al., *Turk. J. Chem.* (2005) 29:255], and 3) a $K_0$ value of 1.31 $cm^2V^{-1}s^{-1}$ reported by the instrument (i.e., Barringer Ion Scan 400A) manufacturer (Smiths Detection, Warren, N.J., U.S.A.). Appearance of the RDX chloride ion cluster (labeled as RDX·Cl⁻) serves to further verify the presence of RDX. The RDX chloride ion cluster is most visible in the one-month sample as a shoulder on the right side of the Cu(dihed) artifact peak that appears at 13.05 ms (see FIG. 16b). Analysis of a standard resulted in an RDX chloride ion cluster with a $K_0$ of 1.39 $cm^2V^{-1}s^{-1}$ (% RSD of 0.07, n=5), a value that agrees with those reported in the literature [e.g., Koyuncu et al., *Turk. J. Chem.* (2005) 29:255] and by the instrument manufacturer (Smiths Detection, Warren, N.J., U.S.A.). This value also corresponds with the shoulder labeled (RDX·Cl⁻) observed in FIGS. 16a and 16b. Comparison to an RDX standard indicated that after one month of exposure, the filter captured approximately 5 ng of RDX. Because of the limited signal and extremely long sampling periods, this demonstration has little practical utility in its present form; however, further research improvements might result in useful applications. The increasing intensity of RDX nitrate ion cluster in the negative ion mobility spectra with increasing sampling times verifies this is gas-phase uptake and not capture of particulates on the filter. A duplicate sample was run to verify these results; overall results were similar.

CONCLUSIONS

Packed column GC experiments were performed on columns packed with inert supports that contained metal β-diketonate polymers. These studies demonstrated high affinity of these polymers toward a wide range of explosives. Capacity factors were used to quantitatively describe the polymer-analyte interaction strength. In general, the relative interaction strength for a given explosive on the metal β-diketonate polymers followed the order Zn(dihed)<Cu(dihed)<<La(dihed). Some interactions were too strong to examine using packed columns. Explosive classes examined included nitro aromatics, nitro alkanes, nitrate esters, and peroxide-based explosives. Selectivity was quantitatively studied by use of the Kováts index. This index value describes where between two n-alkanes an analyte elutes. This is highly relevant since the major matrix interferences in air are non-polar hydrocarbons. The Kováts index for TNT indicated that retention on La(dihed) offered a high degree (4.62 methylene units) of selectivity over the control. Therefore, metal β-diketonate polymer interactions offer both high affinity and selectivity. Selective air sampling using the metal β-diketonate polymer sorbents is expected to be a highly effective method for accomplishing selective trace enrichment of gas-phase explosives from the atmosphere. Other advanced sampling formats such as selective SPME are described herein. These studies combined sampling on a La(dihed)-coated fiber compared to a PDMS control fiber. Proof-of-principle experiments were conducted by sampling in an explosive bunker where the vapor-phase concentration of TNT was less than 3 pptv. Analysis at these low concentrations under realistic conditions is required to find hidden explosives in cargo holds. This study found a nine-fold increase in the quantity of 2,4-DNT captured on the La(dihed) fiber over the PDMS control. In addition a strong signal was generated for TNT on the La(dihed) fiber, whereas this explosive was well below the detection limit on the PDMS control fiber.

Capillary columns can be statically coated with metal p-diketonate polymers to give columns with unique selectivity. A novel azeotrope approach was developed to allow simultaneous SE-30® and lanthanide(dihed) solubility while maintaining a low boiling point. Columns display the expected selective interactions over the control. Strong Lewis bases were selectively retained the most. A range of selective retention was observed with La(dihed)#1 column giving the strongest and Eu(dihed) column giving the weakest selective retention compared to the control column. A number of important applications will be facilitated by this development. Due to a Lewis acid-base retention mechanism that is orthogonal to many GC phases, these separation capillaries would be useful for multidimensional GC separations. Small diameter capillaries (100 μm I.D.) could also be coated to provide fast separations. Importantly, it should be possible to coat multicapillary bundles (about 1000×40 μm I.D. columns bundled together) to provide fast separations with reasonable sample capacity. A short segment (~3-4 cm) of this bundle, or an array of these bundles, could be used for selective sampling of explosives from the air. Precise thermal elution of this array will allow transfer of pure and concentrated fractions to instrumentation for further analysis. Therefore, the MCC array could serve as a powerful selective sampling instrument interface.

The last sampling and analysis approach discussed in this application is the use of deactivated glass fiber filters that are impregnated with metal β-diketonate polymers for selective sampling of explosives. This selective sampling format is combined directly with IMS analysis. This is an example of a streamlined field-deployable approach that eliminates the capillary separation stage and substitutes IMS for mass spectrometry. Studies demonstrated the ability to estimate the vapor-phase TNT concentration in an ammunition magazine and also demonstrated the gas-phase uptake of RDX for the first time. Although some interferences were observed and higher mass resolution would be desirable, the potential of this approach was clearly demonstrated. It is reasonable to expect that with further refinement, this approach can be a useful technology.

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

I claim:

1. A method for coating a separations column for separation and analysis of gas-phase explosives and weaponized chemical agents, comprising the steps of:
    coating a separations column to a preselected uniform thickness with an azeotrope comprising a preselected ratio of a first solvent and at least a second solvent that includes at least one metal β-diketonate polymer and a stationary phase compound dissolved therein, wherein the azeotrope has a boiling point below the first and second solvents, the at least one metal β-diketonate polymer, and the stationary phase compound; and
    forming a stationary phase comprising the stationary phase compound and a preselected concentration of the at least one metal β-diketonate polymer incorporated therein by removing the azeotrope from within the separations column.

2. The method of claim 1, wherein the azeotrope is a binary, a ternary, or a higher order azeotrope.

3. The method of claim 1, wherein the first solvent is methanol.

4. The method of claim 1, wherein the second solvent is methylene chloride.

5. The method of claim 1, wherein the azeotrope comprises methylene chloride and methanol at a preselected ratio of 92.7:7.3 (w/w).

6. The method of claim 1, wherein the stationary phase compound is poly(dimethylsiloxane).

7. The method of claim 1, wherein the azeotrope delivers a concentration of the at least one metal β-diketonate polymer of 0.4% (w/v) in the stationary phase within the separations column.

8. The method of claim 1, wherein the azeotrope includes at least one metal β-diketonate polymer comprising a metal center that is a lanthanide.

9. The method of claim 8, wherein the lanthanide is selected from the group consisting of: La(III), Eu(III), Tb(III), and combinations thereof.

10. The method of claim 1, wherein the azeotrope includes at least one metal β-diketonate polymer comprising a metal center selected from the group consisting of: Cu(II), Ni(II), Zn(II), and combinations thereof.

11. The method of claim 1, wherein the azeotrope includes a metal β-diketonate polymer selected from the group consisting of: La(dihed), Eu(dihed), Tb(dihed), Cu(dihed), Ni(dihed), Zn(dihed), and combinations thereof.

12. The method of claim 1, wherein the coating includes plugging one end of the separations column and puffing a vacuum on the other end of the separations column forming a uniform coating that defines the stationary phase along the interior surface within the separations column.

13. The method of claim 1, wherein the forming includes heating the separations column to a temperature to remove the solvents in the azeotrope that defines the stationary phase along the interior surface within the separations column.

14. The method of claim 1, wherein the coating includes imprinting said metal β-diketonate polymer in the presence of a chemical template selected from the group consisting of: an explosive, a weaponized chemical agent, surrogates thereof, and combinations thereof.

15. A separations column prepared by the process of claim 1.

16. The separations column of claim 15, wherein the separations column is a capillary column.

17. The separations column of claim 15, wherein the separations column is a multi-capillary column.

18. The separations column of claim 15, wherein the separations column is a component of a field-portable analytical device.

19. A method for coating a separations column for separation and analysis of gas-phase explosives and weaponized chemical agents, comprising the steps of:
preparing a coating solution comprising an azeotrope having a preselected ratio of a first solvent and a second solvent, with a preselected concentration of at least one metal β-diketonate polymer and a stationary phase compound dissolved therein, wherein the azeotrope has a boiling point below the first and second solvents, the at least one metal β-diketonate polymer, and the stationary phase compound dissolved therein;
coating a separations column with said coating solution to a preselected thickness therein: and
forming a uniform stationary phase the separations column comprising the stationary phase compound and a preselected concentration of the at least one metal β-diketonate polymer therein by removing the azeotrope.

20. An analytical instrument that includes a separations column prepared by the method of claim 19, wherein the azeotrope is coated on the column to form a stationary phase comprising the metal β-diketonate polymer therein.

21. The analytical instrument of claim 20, wherein the separations column is a multi-capillary array.

22. A sensor that includes a separations column prepared by the method of claim 19, wherein the azeotrope is coated on the column to form a stationary phase comprising the metal β-diketonate polymer therein.

23. The sensor of claim 22, further including a preconcentration device.

24. The sensor of claim 22, wherein the sensor that incorporates said metal β-diketonate polymer is a component of a field-portable analytical device.

* * * * *